United States Patent [19]
Mimura et al.

[11] Patent Number: 5,418,232
[45] Date of Patent: May 23, 1995

[54] DIAZABICYCLOALKENE DERIVATIVES

[75] Inventors: Tetsuya Mimura; Hideo Kubo, both of Tokyo, Japan

[73] Assignee: Daiichi Pharmaceutical Co., Ltd., Tokyo, Japan

[21] Appl. No.: 59,606

[22] Filed: May 12, 1993

[30] Foreign Application Priority Data

May 13, 1992 [JP] Japan .................. 4-120592

[51] Int. Cl.$^6$ .............. A61K 31/53; A61K 31/50; C07D 405/12; C07D 471/04
[52] U.S. Cl. .................. 514/241; 514/242; 514/248; 544/182; 544/215; 544/230; 544/235; 548/423; 548/431; 549/239; 549/387; 549/398; 549/401; 549/405; 549/427
[58] Field of Search .............. 544/230, 235, 182, 215; 514/248, 241

[56] References Cited
U.S. PATENT DOCUMENTS 5,013,853  5/1991  Gericke et al. .............. 544/238
5,112,972  5/1992  Gericke et al. .............. 544/238

FOREIGN PATENT DOCUMENTS 0012366  6/1980  European Pat. Off. .
0068310  1/1983  European Pat. Off. .
0089528  9/1983  European Pat. Off. .
0117403  9/1984  European Pat. Off. .
0167995  1/1986  European Pat. Off. .
0231744  8/1987  European Pat. Off. .
0340718  11/1989  European Pat. Off. .
0363883  4/1990  European Pat. Off. .
2-145584  6/1990  Japan .
3-20275  1/1991  Japan .

OTHER PUBLICATIONS

Bergmann et al *Journal of Medicinal Chemistry*, vol. 33, pp. 2759–2767 (1990).
3–Methyl–2H–1–benzopyran Potassium Channel Activators, Rolf Gericke et al, J. Med. Chem. 1991, 34, 3074–3085.

*Primary Examiner*—Emily Bernhardt
*Attorney, Agent, or Firm*—Sughrue, Mion, Zinn, Macpeak & Seas

[57] ABSTRACT

A compound of formula (I) possesses excellent potassium channel opening activity and is effective on various diseases arising from contractions of blood vessels, bronchial smooth muscles, etc., for example, ischemic heart diseases exemplified by angina pectoris, asthma, pollakisuria, sequela of subarachnoid hemorrhage, peripheral arterioinfarct, and so on. The compound has potent and long-lasting antihypertensive activity, with the onset of the action being slow, excellent activity in increasing renal blood flow, and high safety, and is therefore particularly useful as an antihypertensive.

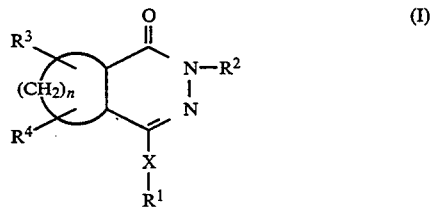

(I)

The substituents are as defined in the specification.

6 Claims, No Drawings

DIAZABICYCLOALKENE DERIVATIVES

FIELD OF THE INVENTION

The present invention relates to a novel diazabicycloalkene compound having excellent potassium channel opening activity and to treating agents for hypertension, angina pectoris, and asthma which contain the diazabicycloalkene compound as an active ingredient.

BACKGROUND OF THE INVENTION

Hypertension is treated by maintaining a patient on an antihypertensive drug for a long time and, therefore, antihypertensive drugs are demanded not only to exhibit potent antihypertensive activity but to cause no undesirable side effects throughout the long-term administration. That is, antihypertensive drugs are required (1) to have potent and long-lasting antihypertensive activity; (2) to show slow onset of antihypertensive action because quick onset of the action will significantly change the homeostatis of circulatory organs (see *Life Science*, Vol. 47, pp. 1693–1705 (1990)), readily causing reflex tachycardia (see *Japanese Journal of Pharmacology*, Vol. 58 (Suppl. 1), p. 36 (1992)); and desirably (3) to increase the renal blood flow because a blood flow disorder in the kidney closely relates to the maintenance and progress of hypertension and an increase in renal blood flow is expected to alleviate hypertension (see *Circulation*, Vol. 69, pp. 1142–1145 (1984)).

A compound represented by formula (IV):

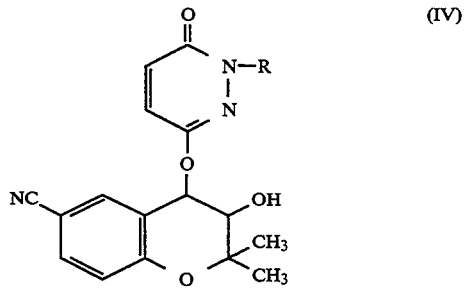

wherein R represents a hydrogen atom, an alkyl group, an aryl group, an aralkyl group, etc., is known to exhibit potent and long-lasting antihypertensive activity attributed to potassium channel activation and therefore be useful as an antihypertensive drug (see JP-A-2-145584, JP-A-3-20275, and *Journal of Medicinal Chemistry*, Vol. 33, pp. 2759–2767 (1990); the term "JP-A" as used herein means an "unexamined published Japanese patent application").

Although the compounds of formula (IV) almost satisfy the requirements for potency and duration of antihypertensive activity, they are still unsatisfactory in terms of the pattern of onset of antihypertensive action and renal blood flow increasing activity.

SUMMARY OF THE INVENTION

An object of the present invention is to provide a compound which has potent and long-lasting antihypertensive activity, shows slow onset of the action, and also exhibits excellent activity in increasing the renal blood flow.

Another object of the present invention is to provide pharmaceuticals containing the compound.

In the light of the above-mentioned present situation, the present inventors have synthesized various diazabicycloalkene compounds and investigated their pharmacological activities. As a result, they have found that a diazabicycloalkene compound represented by formula (I) shown below has excellent potassium channel opening activity and potent and long-lasting antihypertensive activity with slow onset, and possesses a strong activity for increasing the renal blood flow and is therefore useful as a treating agent for hypertension. The present inventors have also found that the compound of formula (I) is useful as a treating agent for other diseases caused by contractions of blood vessels or bronchial smooth muscles, such as angina pectoris and asthma. The present invention has been completed based on these findings.

The present invention relates to a diazabicycloalkene compound represented by formula (I):

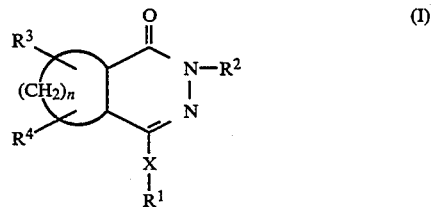

wherein $R^1$ represents a group represented by formula (II) or (III):

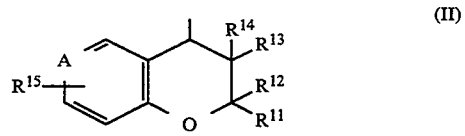

wherein $R^{11}$ and $R^{12}$ each represents a lower alkyl group, or they are taken together to form a lower alkylene group; $R^{13}$ represents a hydroxyl group, a lower acyloxy group or a lower alkoxy group; $R^{14}$ represents a hydrogen atom or a lower alkyl group; A represents a nitrogen atom or C—$R^{16}$; $R^{15}$ and $R^{16}$ each represents a hydrogen atom, a halogen atom, a cyano group, a nitro group, a trifluoromethoxy group, a pentafluoroethyl group, a lower alkyl group, a lower alkenyl group, a lower alkynyl group, a lower acyl group, a carboxyl group, a lower alkoxycarbonyl group, a carbamoyl group which may be substituted with a lower alkyl group having 1 or 2 carbon atoms, a sulfinyl or sulfonyl group which may be substituted with a lower alkyl, lower alkoxy, aryl or aryloxy group, or a sulfamoyl group which may be substituted with a lower alkyl group having 1 or 2 carbon atoms:

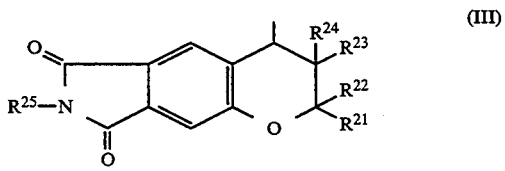

wherein $R^{21}$ and $R^{22}$ each represents a lower alkyl group, or they are taken together to form a lower alkylene group; $R^{23}$ represents a hydroxyl group, a lower acyloxy group or a lower alkoxy group; $R^{24}$ represents a hydrogen atom or a lower alkyl group;

$R^{25}$ represents a hydrogen atom, a lower alkyl group, a lower alkenyl group, a lower alkynyl group, an aralkyl group, or an aralkyl group having at least one hetero atom at the aryl moiety; X represents an oxygen atom, a sulfur atom or $N-R^{31}$, wherein $R^{31}$ represents a hydrogen atom, a lower alkyl group, a lower acyl group or an aralkyl group; $R^2$ represents a hydrogen atom, a lower alkenyl group, a lower alkynyl group, a substituted or unsubstituted lower alkyl group, a substituted or unsubstituted aryl group, a substituted or unsubstituted aralkyl group, or an aralkyl group having at least one hetero atom at the aryl moiety; $R^3$ and $R^4$ each represents a hydrogen atom, a halogen atom or a lower alkyl group; and n represents 1 or 2.

The present invention also relates to a treating agent and to compositions for treating for hypertension, angina pectoris or asthma which contains the diazabicycloalkene compound of formula (I) as an active ingredient.

DETAILED DESCRIPTION OF THE INVENTION

In formula (I), and in the following discussion of formula (I), each of the named groups are unsubstituted groups unless they are specifically referred to as including substituted groups.

The various groups mentioned in formula (I) are described in further detail below.

The "lower alkyl group" includes straight chain or branched alkyl groups having from 1 to 6 carbon atoms, e.g., a methyl group, an ethyl group, a propyl group, an isopropyl group, a butyl group, and a t-butyl group.

The "lower alkenyl group" includes straight chain or branched alkenyl groups containing from 2 to 6 carbon atoms, e.g., a vinyl group and a propenyl group.

The "lower alkynyl group" includes straight chain or branched alkynyl groups containing from 2 to 6 carbon atoms, e.g., an ethynyl group, a 1-propynyl group, and a 2-propynyl group.

The "lower alkylene group" includes those containing from 2 to 6 carbon atoms, e.g., a propylene group, a butylene group, a pentylene group, and a hexylene group.

The "aralkyl group" includes a benzyl group, a phenylethyl group, and a naphthylmethyl group.

The "aralkyl group having at least one hetero atom at the aryl moiety" includes a 5- to 6-membered heterocyclic ring containing at least one hetero atom (preferably 1 to 3 hetero atoms) selected from a nitrogen atom, an oxygen atom or a sulfur atom, which ring is bonded to an alkylene group containing from 1 to 4 carbon atoms. The ring can contain, for example, one to three nitrogen atoms. Specific examples thereof are pyridylmethyl, pyridylethyl, pyrimidinylmethyl, pyrimidinylethyl, piperazinylmethyl, piperazinylethyl, triazinylmethyl, triazinylethyl, pyrazolylmethyl, pyrazolylethyl, pyrazolylpropyl, imidazolylmethyl, imidazolylethyl, imidazolylpropyl, oxazolylmethyl, oxazolylethyl, oxazolylpropyl, isoxazolylmethyl, isoxazolylethyl, isoxazolylpropyl, thiazolylmethyl, thienylmethyl, aziridinylmethyl, and aziridinylethyl groups.

The "aryl group" includes a phenyl group, a naphthyl group, and a biphenyl group.

The "lower alkoxy group" includes those containing from 1 to 4 carbon atoms, e.g., a methoxy group, an ethoxy group, a propoxy group, and a butoxy group.

The "lower acyl group" includes those containing from 1 to 8 carbon atoms, e.g., a formyl group, an acetyl group, a propanoyl group, and a butanoyl group.

The "lower acyloxy group" includes those containing from 1 to 8 carbon atoms, e.g., a formyloxy group, an acetoxy group, a propanoyloxy group, and a butanoyloxy group.

The "lower alkoxycarbonyl group" includes those containing from 2 to 6 carbon atoms, e.g., a methoxycarbonyl group, an ethoxycarbonyl group, and a propoxycarbonyl group.

The "sulfinyl group which may be substituted with a lower alkyl group", that is, a lower alkylsulfinyl group, includes those containing from 1 to 5 carbon atoms, e.g., a methylsulfinyl group, an ethylsulfinyl group, and a propylsulfinyl group.

The "sulfonyl group which may be substituted with a lower alkyl group", that is, a lower alkylsulfonyl group, includes those containing from 1 to 5 carbon atoms, e.g., a methylsulfonyl group, an ethylsulfonyl group, and a propylsulfonyl group.

The "sulfonyl group which may be substituted with a lower alkoxy group", that is, a lower alkoxysulfonyl group", includes those containing from 1 to 5 carbon atoms, e.g., a methoxysulfonyl group, an ethoxysulfonyl group, and a propoxysulfonyl group.

The "sulfinyl group which may be substituted with a lower alkoxy group" includes those containing from 1 to 5 carbon atoms, e.g., a methoxysulfinyl group, an ethoxysulfinyl group, and a propoxysulfinyl group.

The "sulfonyl group which may be substituted with an aryl group" includes a phenylsulfonyl group and a naphthylsulfonyl group.

The "sulfinyl group which may be substituted with an aryl group" includes a phenylsulfinyl group and a naphthylsulfinyl group.

The "sulfonyl group which may be substituted with an aryloxy group" includes a phenyloxysulfonyl group and a naphthyloxysulfonyl group.

The "sulfinyl group which may be substituted with an aryloxy group" includes a phenyloxysulfinyl group and a naphthyloxysulfinyl group.

The "halogen atom" includes a fluorine atom, a chlorine atom, a bromine atom, and an iodine atom.

When $R^2$ is a substituted lower alkyl group, representative examples thereof include a formyl substituted-lower alkyl group, a carboxyl substituted-lower alkyl group, a hydroxyl substituted-lower alkyl group, a lower alkoxy substituted-lower alkyl group, a lower acyl substituted-lower alkyl group, a lower alkoxycarbonyl substituted-lower alkyl group, a lower acyloxy substituted-lower alkyl group, a halogen substituted-lower alkyl group, a nitro substituted-lower alkyl group, a cyano substituted-lower alkyl group, a lower alkylsulfonyl substituted-lower alkyl group, a lower alkylsulfinyl substituted-lower alkyl group, an arylsulfonyl substituted-lower alkyl group, an arylsulfinyl substituted-lower alkyl group, a sulfamoyl substituted-lower alkyl group, a mono-lower alkylsulfamoyl substituted-lower alkyl group, a di-lower alkylsulfamoyl substituted-lower alkyl group, a carbamoyl substituted-lower alkyl group, a mono-lower alkylcarbamoyl substituted-lower alkyl group, a di-lower alkylcarbamoyl substituted-lower alkyl group, an amino substituted-lower alkyl group, a mono-lower alkylamino substituted-lower alkyl group, a di-lower alkylamino substituted-lower alkyl group, a mercapto substituted-lower alkyl group, a lower alkylthio substituted-lower alkyl group, an arylthio substituted-lower alkyl group, a lower acylamino substituted-lower alkyl group, and a trifluoromethoxy substituted-lower alkyl group.

When $R^2$ is a substituted aryl group, representative examples thereof include a formylaryl group, a carboxyaryl group, a lower alkoxyaryl group, a lower acylaryl group, a lower alkoxycarbonylaryl group, a lower acyloxyaryl group, a halogenoaryl group, a nitroaryl group, a cyanoaryl group, a lower alkylsulfonylaryl group, a lower alkylsulfinylaryl group, an arylsulfonylaryl group, an arylsulfinylaryl group, a sulfamoylaryl group, a mono-lower alkylsulfamoylaryl group, a di-lower alkylsulfamoylaryl group, a carbamoylaryl group, a mono-lower alkylcarbamoylaryl group, a di-lower alkylcarbamoylaryl group, an aminoaryl group, a mono-lower alkylaminoaryl group, a di-lower alkylaminoaryl group, a mercaptoaryl group, a lower alkylthioaryl group, an arylthioaryl group, a lower acylaminoaryl group, and a trifluoromethoxyaryl group.

When $R^2$ is a substituted aralkyl group, representative examples thereof include those having the aryl moiety thereof substituted with a halogen atom, a lower alkyl group, a hydroxyl group, a lower alkoxy group, a cyano group, a lower acyl group, a lower alkoxycarbonyl group, a nitro group, a trifluoromethoxy group, a lower alkylsulfinyl group, a lower alkylsulfonyl group, a lower alkoxysulfonyl group, a lower alkoxysulfinyl group, a carbamoyl group, a mono-lower alkylcarbamoyl group, a di-lower alkylcarbamoyl group, a sulfamoyl group, a mono- or di-lower alkylsulfamoyl group, or a carboxyl group.

The compound of formula (I) can be converted in a usual manner to a pharmaceutically acceptable salt by treatment with an inorganic acid (e.g., hydrochloric acid, sulfuric acid, hydrobromic acid, phosphoric acid or nitric acid) or an organic acid (e.g., acetic acid, propionic acid, succinic acid, glycolic acid, lactic acid, malic acid, tartaric acid, citric acid, maleic acid, fumaric acid, methanesulfonic acid, p-toluenesulfonic acid or ascorbic acid) or to a hydrate or various solvates.

Of the compounds of formula (I), those wherein $R^1$ represents the group of formula (II) are preferred. In formula (II), $R^{11}$ and $R^{12}$ are each preferably a methyl group; $R^{13}$ is preferably a hydroxyl group or a lower acyloxy group; $R^{14}$ is preferably a hydrogen atom or a methyl group; $R^{15}$ is preferably a hydrogen atom; and A is preferably C—$R^{16}$, wherein $R^{16}$ is preferably a cyano group, a nitro group or a pentafluoroethyl group.

$R^2$ is preferably a hydrogen atom, a methyl group, an ethyl group, a propyl group, a 2-propynyl group, an isobutyl group, an allyl group, an unsubstituted benzyl group, or a benzyl group having as a substituent a lower alkyl group containing from 1 to 4 carbon atoms, a halogen atom, an alkoxy group or a cyano group attached at the phenyl moiety of the benzyl group.

$R^3$ and $R^4$ are each preferably a hydrogen atom. X is preferably an oxygen atom. n is preferably 1.

The compounds of formula (I) each include optical isomers represented by formulae (Ia) to (Id) shown below, assigned to the asymmetric carbon atoms. These optically active compounds and mixtures thereof are also included under the scope of the present invention. Particularly preferred optically active compounds are those represented by formula (Ia) or (Ib). For example, the compound synthesized in Example 21 hereinafter described is included under formula (Ia). Particularly preferred mixtures of optically active compounds are a racemic mixture of the compound of formula (Ia), and the compound of formula (Ic), and a racemic mixture of the compound of formula (Ib) and the compound of formula (Id):

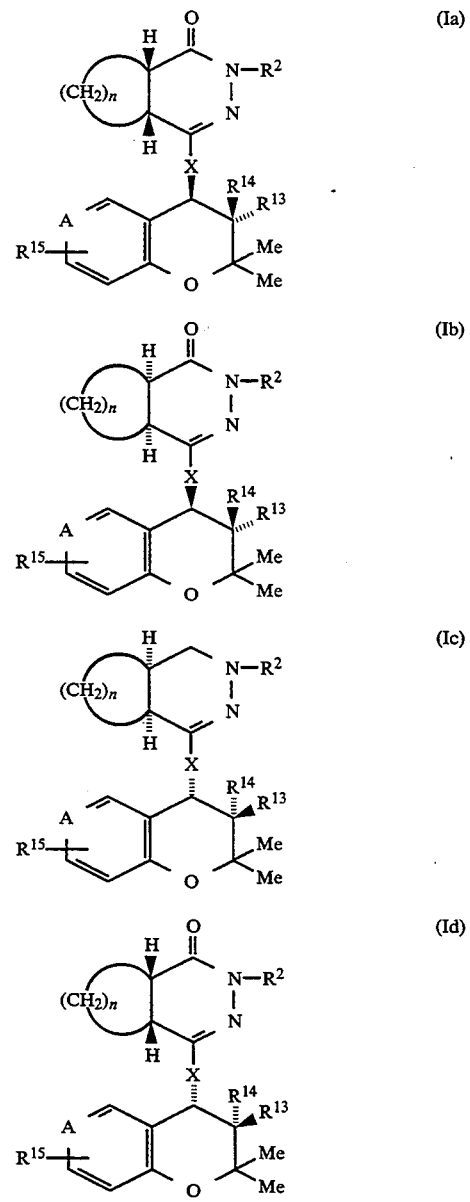

wherein $R^2$, $R^{13}$, $R^{14}$, $R^{15}$, A, X, and n are as defined above in formula (I).

Specific examples of the compounds of formula (I) are shown below.

3,4-trans-4-(3-Benzyl-2-oxo-3,4-diazabicyclo[4.1.0]-hept-4-en-5-yloxy)-3,4-dihydro-2,2-dimethyl-3-hydroxy-2H-1-benzopyran-6-carbonitrile:

A racemate of (Ia) and (Ic) or a racemate of (Ib) and (Id), wherein $R^2$=benzyl; $R^{13}$=OH; $R^{14}$=$R^{15}$=H; A=C—CN; n=1; and X=O 3,4-trans-3,4-Dihydro-2,2-dimethyl-3-hydroxy-4-(3-methyl-2-oxo-3,4-diazabicyclo[4.1.0]hept-4-en-5-yloxy)-2H-1-benzopyran-6-carbonitrile:

A racemate of (Ia) and (Ic) or a racemate of (Ib) and (Id), wherein $R^2$=$CH_3$; $R^{13}$=OH; $R^{14}$=$R^{15}$=H; A=C—CN; n=1; and X=O 3,4-trans-3,4-Dihydro-2,2-dimethyl-3-hydroxy-4-(3-methyl-2-oxo-3,4-diazabicyclo[4.1.0]hept-4-en-5-yloxy)-2H-1-benzopyran-6,7-dicarboxyimide:

A racemate of (Ie) and (Ig) or a racemate of (If) and (Ih):

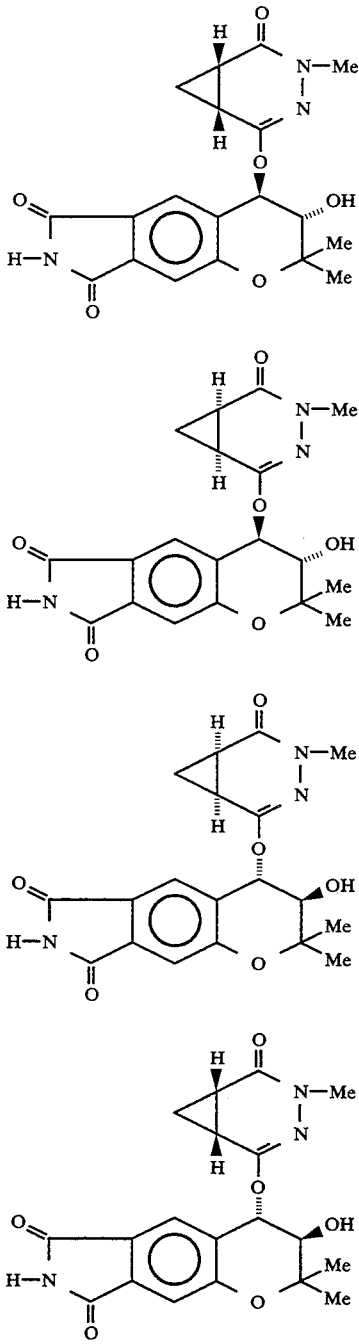

4) (3S,4R,1'S,6'R)-4-(3-Benzyl-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia), wherein $R^2$=benzyl; $R^{13}$=OH; $R^{14}$, $R^{15}$=H; A=C—CN; n=1; and X=O 5) (3S,4R,1'R*,6'S*)-3,4-Dihydro-2,2-dimethyl-3-hydroxy-4-(3-methyl-2-oxo-3,4-diazabicyclo[4.1.0]hept-4-en-5-yloxy)-2H-1-benzopyran-6-carbonitrile:

An optically active compound (Ia) or (Ib), wherein $R^2$=CH$_3$; $R^{13}$=OH; $R^{14}$, $R^{15}$=H; A=C—CN; n=1; and X=O 6) (3S,4R,1'R*,6'S*)-4-(3-Allyl-2-oxo-3,4-diazabicyclo-[4.1.0]hept-4-en-5-yloxy)-3,4-dihydro-2,2-dimethyl-3-hydroxy-2H-1-benzopyran-6-carbonitrile:

An optically active compound (Ia) or (Ib), wherein $R^2$=allyl; $R^{13}$=OH; $R^{14}$=$R^{15}$=H; A=C—CN; n=1; and X=O 7) (3S,4R,1'R*,6'S*)-3,4-Dihydro-2,2-dimethyl-3-hydroxy-4-(2-oxo-3-(2-propyn-1-yl)-3,4-diazabicyclo[4.1.0]hept-4-en-5-yloxy)-2H-1-benzopyran-6-carbonitrile:

An optically active compound (Ia) or (Ib), wherein $R^2$=2-propyn-1-yl; $R^{13}$=OH; $R^{14}$=$R^{15}$=H; A=C—CN; n=1; and X=O 8) (3S,4R,1'R*,6'S*)-3,4-Dihydro-2,2-dimethyl-3-hydroxy-4-(3-(2-methoxyethyl)-2-oxo-3,4-diazabicyclo[4.1.0]hept-4-en-5-yloxy)-2H-1-benzopyran-6-carbonitrile:

An optically active compound (Ia) or (Ib), wherein $R^2$=2-methoxyethyl; $R^{13}$=OH; $R^{14}$=$R^{15}$=H; A=C—CN; n=1; and X=O 9) (3S,4R,1'R*,6'S*)-3,4-Dihydro-2,2-dimethyl-3-hydroxy-4-(3-(2-hydroxyethyl)-2-oxo-3,4-diazabicyclo[4.1.0]hept-4-en-5-yloxy)-2H-1-benzopyran-6-carbonitrile:

An optically active compound (Ia) or (Ib), wherein $R^2$=2-hydroxyethyl; $R^{13}$=OH; $R^{14}$=$R^{15}$=H; A=C—CN; n=1; and X=O 10) (3S,4R,1'R*,6'S*)-3,4-Dihydro-2,2-dimethyl-3-hydroxy-4-(3-isobutyl-2-oxo-3,4-diazabicyclo[4.1.0]hept-4-en-5-yloxy)-2H-1-benzopyran-6-carbonitrile:

An optically active compound (Ia) or (Ib), wherein $R^2$=isobutyl; $R^{13}$=OH; $R^{14}$=$R^{15}$=H; A=C—CN; n=1; and X=O 11) (3S,4R,1'R*,6'S*)-4-(3-n-Butyl-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia) or (Xb), wherein $R^2$=n-butyl; $R^{13}$=OH; $R^{14}$=$R^{15}$=H; A=C—CN; n=1; and X=O 12) (3S, 4R, 1'R*, 6'S*)-4-(3-(2-Chlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia) or (Ib), wherein $R^2$=2-chlorobenzyl; $R^{13}$=OH; $R^{14}$=$R^{15}$=H; A=C—CN; n=1; and X=O 13) (3S,4R,1'R*,6'S*)-4-(3-(2,6-Dichlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia) or (Ib), wherein $R^2$=2,6-dichlorobenzyl; $R^{13}$=OH; $R^{14}$=$R^{15}$=H; A=C—CN; n=1; and X=O 14) (3S,4R,1'R*,6'S*)-4-(3-(2,4-Dichlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia) or (Ib), wherein $R^2$=2,4-dichlorobenzyl; $R^{13}$=OH; $R^{14}$=$R^{15}$=H; A=C—CN; n=1; and X=O 15) (3S,4R,1′R*,6′S*)-3,4-Dihydro-2,2-dimethyl-3-hydroxy-4-(3-(2-methylbenzyl)-2-oxo-3,4-diazabicyclo[4.1.0]hept-4-en-5-yloxy)-2H-1-benzopyran-6-carbonitrile:

An optically active compound (Ia) or (Ib), wherein $R^2$=2-methylbenzyl; $R^{13}$=OH; $R^{14}$=$R^{15}$=H; A=C—CN; n=1; and X=O 16) (3S,4R,1′R*,6′S*)-3,4-Dihydro-2,2-dimethyl-3-hydroxy-4-(2-oxo-3,4-diazabicyclo[4.1.0]hept-4-en-5-yloxy)-2H-1-benzopyran-6-carbonitrile:

An optically active compound (Ia) or (Ib), wherein $R^2$=H; $R^{13}$=OH; $R^{14}$=$R^{15}$=H; A=C—CN; n=1; and X=O 17) (3S,4R,1′R*,6′S*)-4-(3-Cyanomethyl-2-oxo-3,4-diazabicyclo[4.1.0]hept-4-en-5-yloxy)-3,4-dihydro-2,2-dimethyl-3-hydroxy-2H-1-benzopyran-6-carbonitrile:

An optically active compound (Ia) or (Ib), wherein $R^2$=cyanomethyl; $R^{13}$=OH; $R^{14}$=$R^{15}$=H; A=C—CN; n=1; and X=O 18) (3S,4R,1′R*,6′S*)-3,4-Dihydro-2,2-dimethyl-4-(3-ethoxycarbonylmethyl-2-oxo-3,4-diazabicyclo[4.1.0]-hept-4-en-5-yloxy)-3-hydroxy-2H-1-benzopyran-6-carbonitrile:

An optically active compound (Ia) or (Ib), wherein $R^2$=ethoxycarbonylmethyl; $R^{13}$=OH; $R^{14}$=$R^{15}$=H; A=C—CN; n=1; and X=O 19) (3S,4R,1′R*,6′S*)-3,4-Dihydro-3-hydroxy-4-(3-methyl-2-oxo-3,4-diazabicyclo[4.1.0]hept-4-en-5-yloxy)-2,2,3-trimethyl-2H-1-benzopyran-6-carbonitrile:

An optically active compound (Ia) or (Ib), wherein $R^2$=$R^{14}$=CH$_3$; $R^{13}$=OH; $R^{15}$=H; A=C—CN; n=1; and X=O pyran-6-carbonitrile:
An optically active compound (Ia) or (Ib), wherein $R^2$=2-methylbenzyl; $R^{13}$=OH; $R^{14}$=$R^{15}$=H; A=C—CN; n=1; and X=O The compounds of the present invention can be prepared according to Processes (a) to (c) described below.

Process (a):

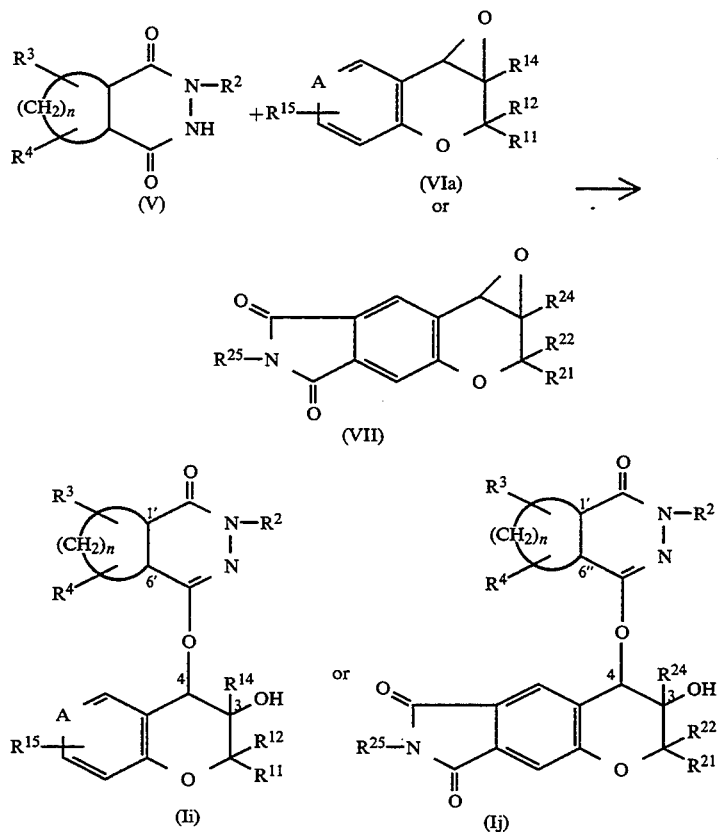

wherein $R^2$, $R^3$, $R^4$, $R^{11}$, $R^{12}$, $R^{14}$, $R^{15}$, $R^{21}$, $R^{22}$, $R^{24}$, $R^{25}$, n and A are as defined above in formula (I).

Compound (Ii) or compound (Ij) can be prepared by reacting compound (V) with compound (VIa) or compound (VII), respectively.

The reaction is usually carried out in an inert solvent, such as a lower aliphatic alcohol (e.g., methyl alcohol or ethyl alcohol), acetonitrile or dimethylformamide (DMF), preferably ethyl alcohol or DMF, in the presence of an organic base (e.g., pyridine) or an inorganic base (e.g., sodium hydroxide or potassium carbonate), preferably pyridine, as a catalyst at a temperature of from 50° to 150° C., preferably from 80° to 110° C., for a period of from 5 to 48 hours, preferably from 10 to 20 hours.

Whether the starting compound (VIa) or (VII) is a racemate or an optically active compound decides whether the resulting compound (Ii) or (Ij) is a racemate or an optically active compound.

The racemate of compound (VIa) can be obtained by the process disclosed in JP-A-52-122372 or JP-A-61-293984. Of compounds (VIa), compound (VIb) having a (3S,4S) configuration can be synthesized by the process disclosed in JP-A-2-42074 or *Journal of Medicinal Chemistry*, Vol. 34, p. 3074 (1991). Starting with the optically active compound (VIb) shown below, there is obtained compound of formula (Ik) as follows:

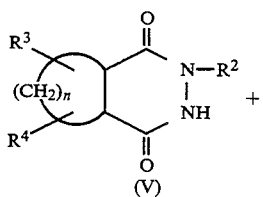

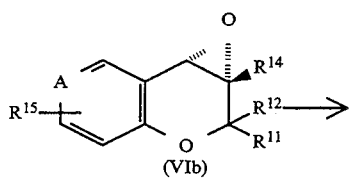

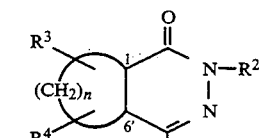

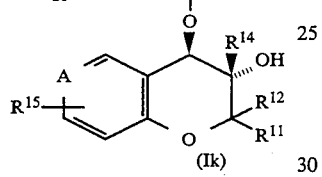

wherein $R^2$, $R^3$, $R^4$, $R^{11}$, $R^{12}$, $R^{14}$, $R^{15}$, n and A are as defined above in formula (I).

Compound (Ii) obtainable by using compound (VIa) embraces 4 optical isomers assigned to the trans configuration of the 3,4-positions of the pyran ring and the cis-α- or β-configuration of the hydrogen atoms bonded to the 1'- and 6'-positions of the diazabicycloalkene ring. The four optical isomers are composed of two pairs of antipodes. Racemates of each of the two pairs of antipodes can easily be resolved by silica gel column chromatography.

Compound (Ik) which is obtained by using compound (VIb) embraces 2 diastereomers assigned to the configuration of the hydrogen atoms bonded to the 1'- and 6'-positions of the diazabicycloalkene ring. The two diastereomers can easily be separated by column chromatography on silica gel.

Compound (V) which is used in the above reaction scheme is obtained by reacting compound (VIII) shown below with a hydrazine derivative in a lower aliphatic alcohol (e.g., methyl alcohol or ethyl alcohol), acetonitrile, acetic acid, etc.

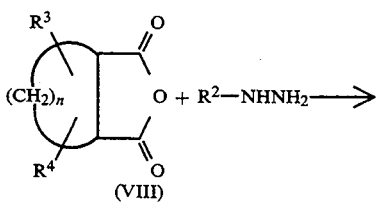

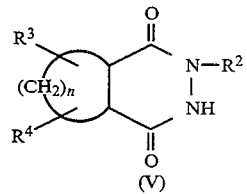

wherein $R^2$, $R^3$, $R^4$, and n are as defined above in formula (I).

Compound (VIII) is obtained by a process disclosed in the literature. For example, compound (VIII) wherein n=1 is prepared according to *Justus Liebigs Annalen der Chemie*, Vol. 606, p. 1 (1957), *Tetrahedron Letters*, Vol. 21, p. 1847 (1978) or *ibid.*, Vol. 28, p. 267 (1987), and compound (VIII) wherein n=2 is prepared according to *Tetrahedron Letters*, Vol. 28, p. 267 (1987).

It is possible to displace the substituent $R^2$ on a specific compound of formula (V) with other desired substituents in a known manner, for example, by catalytic reduction or dealkylation.

Process (b):

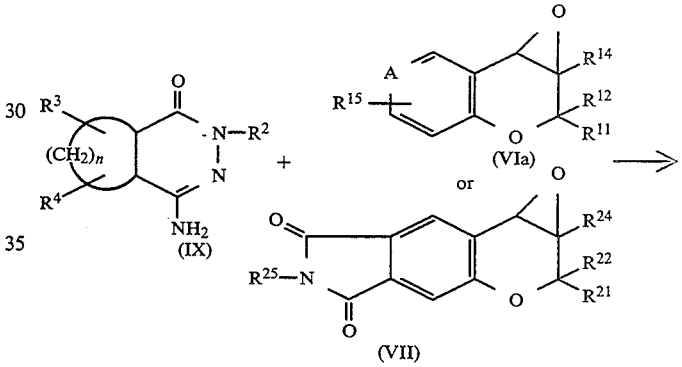

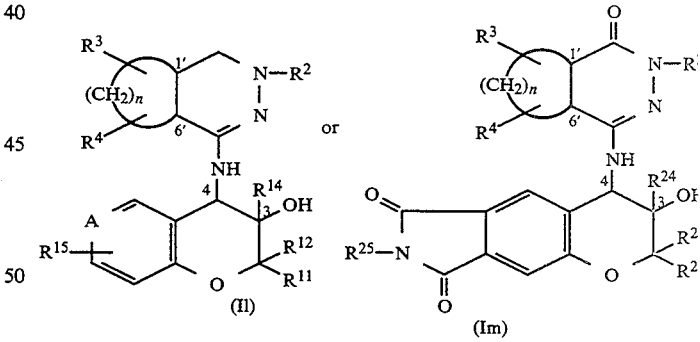

wherein $R^2$, $R^3$, $R^4$, $R^{11}$, $R^{12}$, $R^{14}$, $R^{15}$, $R^{21}$, $R^{22}$, $R^{24}$, $R^{25}$, n and A are as defined above in formula (I).

Compound (II) or (Im) can be prepared by reacting compound (IX) with compound (VIa) or (VII).

The reaction is carried out in an inert solvent, such as a lower aliphatic alcohol (e.g., methyl alcohol or ethyl alcohol), acetonitrile or DMF, preferably DMF, in the presence of an organic base (e.g., pyridine) or an inorganic base (e.g., sodium hydroxide, potassium carbonate or sodium hydride), preferably sodium hydride, as a catalyst at a temperature of from 20° to 150° C., preferably from 50° to 110° C., for a period of from 5 to 48 hours, preferably from 10 to 20 hours.

Compound (IX) can be synthesized according to the process disclosed, e.g., in *Journal of Heterocyclic Chem-* istry, Vol. 21, pp. 961-968 (1984), *Journal of Organic Chemistry*, Vol. 36, pp. 3356-3361 (1971), or *Chemische Berichte*, Vol. 100, pp. 2719-2729 (1967).

Similarly to process (a), whether the starting compound (VIa) or (VII) is a racemate or an optically active compound decides whether the resulting compound (Il) or (Im) is a racemate or an optically active compound. Where starting with a racemate, the resulting compound (II) embraces 4 optical isomers assigned to the trans configuration of the 3,4-positions of the pyran ring and the cis-α- or β-configuration of the hydrogen atoms bonded to the 1'- and 6'-positions of the diazabicycloalkene ring. The four optical isomers are composed of two pairs of antipodes. Racemates of each of the two pairs of antipodes can easily be resolved by silica gel column chromatography.

On the other hand, the compound which is obtained by starting with compound (VIb) embraces 2 diastereomers assigned to the configuration of the hydrogen atoms bonded to the 1'- and 6'-positions. The two diastereomers can easily be separated by column chromatography on silica gel.

In either of processes (a) and (b), the substituent $R^2$ of the resulting compound may be displaced, if desired, with other desired substituents in a known manner. For example, a compound wherein $R^2$ is a hydrogen atom can be obtained from the corresponding compound wherein $R^2$ is a commonly employed releasable group, e.g., a p-methoxybenzyl group, by reacting with a releasing reagent, e.g., 2,3-dichloro-5,6-dicyano-1,4-benzoquinone (DDQ). Further, a compound wherein $R^2$ is a hydrogen atom may be converted to the corresponding compounds having various substituents as $R^2$ by reacting with various halogen compound.

Process (c):

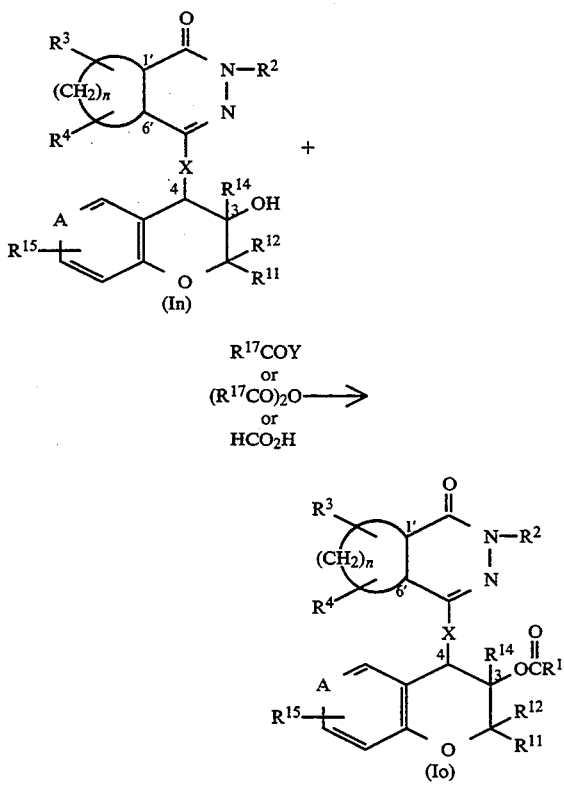

wherein $R^2$, $R^3$, $R^4$, $R^{11}$, $R^{12}$, $R^{14}$, $R^{15}$, X, A, and n are as defined above in formula (I); $R^{17}$ represents a lower alkyl group; $R^{18}$ represents a hydrogen atom or a lower alkyl group; and Y represents a halogen atom.

That is, compound (Io) is prepared by reacting compound (In) obtainable by process (a) or (b) with an acylating agent in accordance with the process disclosed in JP-A-3-20275. Suitable acylating agents which can be used preferably include a lower alkylcarboxylic acid anhydride, a lower alkylcarboxylic acid halide, and formic acid. The acylation reaction is carried out in an inert solvent (e.g., methylene chloride, tetrahydrofuran (THF) or DMF), preferably methylene chloride, in the presence of an inorganic base (e.g., potassium carbonate) or an organic base (e.g., pyridine or triethylamine), preferably triethylamine, as a catalyst at a temperature of from 20° to 150° C., preferably from 20° to 80° C., for a period of from 1 to 48 hours, preferably from 3 to 20 hours.

In process (c), where compound (Ij) or (Im) is used as a starting compound, compounds of formula (I) wherein $R^1$ has the structure of formula (III) are obtained.

The compounds of the present invention can be obtained as a pure optical isomer by processes (a) to (c) wherein an optically active compound is used as a starting material, or wherein a racemate is used as a starting material, and the resulting isomeric mixture is resolved by an appropriate combination of resolution techniques, such as column chromatography, optical resolution with an optical resolving agent, utilization of a difference between two diastereomers in solubility in a solvent, and HPLC.

The compounds of formula (I) are sometimes isolated in the form of a hydrate or a solvate or as an amorphous compound, and all of these modifications are included under the scope of the present invention.

The thus prepared compound of formula (I) possesses excellent potassium channel opening activity and is therefore effective on various diseases arising from contractions of blood vessels, bronchial smooth muscles, etc., for example, ischemic heart diseases exemplified by angina pectoris, asthma, pollakisuria, sequela of subarachnoid hemorrhage, peripheral arterioinfarct, and so on. The compound has potent and long-lasting antihypertensive activity, with the onset of the action being slow, and exhibits excellent activity of increasing the renal blood flow. Besides, the compound is of high safety. Accordingly, the compound is particularly useful as a treating agent for hypertension.

The compound of the present invention can be administered orally or non-orally in any desired dose form, such as tablets, granules, powders, capsules, solution, syrups, oily or aqueous suspensions, and the like. In the preparations of the dosage forms and compositions containing the compound, commonly employed vehicles or adjuvants, such as lubricants, solvents, and surface active agents, may be added.

The dose of the compound usually is from 0.001 to 1.0 mg, more preferably from 0.01 to 0.5 mg, per day for a human adult in oral administration, though somewhat varying depending on the administration route, symptoms, and administration period.

The present invention will now be illustrated in greater detail with reference to Reference Examples, Examples, and Test Examples, but it should be understood that the present invention is not construed as being limited thereto.

REFERENCE EXAMPLE 1

(±)-3-Benzyl-3,4-diazabicyclo[4.1.0]heptane-2,5-dione

In 150 ml of acetonitrile was dissolved 42 g (374 mmol) of 1,2-cyclopropanedicarboxylic acid anhydride, and to the solution was added dropwise a solution of 45.8 g (374 mmol) of benzylhydrazine in 50 ml of acetonitrile, and the mixture was heated under reflux for 15 hours. The solvent was removed by distillation under reduced pressure, and the residue was purified by silica gel column chromatography. Crystallization from ethyl acetate gave 24.1 g (29.7%) of the titled compound.

Melting Point: 186°–188° C.

NMR (CDCl$_3$, TMS) δppm: 1.15 (1H, m), 1.69 (1H, m), 2.10 (1H, m), 2.28 (1H, m), 4.66 (1H, d, J=15.6 Hz), 4.84 (1H, d, J=15.6 Hz), 7.32 (5H, s)

REFERENCE EXAMPLES 2 TO 24

Compounds shown in Table 1 below were synthesized in the same manner as in Reference Example 1.

TABLE 1

| Reference Example No. | Compound | Melting Point (°C.) | NMR Data (CDCl$_3$, TMS), δ (ppm) |
|---|---|---|---|
| 2 | (±)-3-methyl-3,4-diazabicyclo[4.1.0]heptane-2,5-dione | 195–196 | 1.21(1H, m), 1.71(1H, m), 2.12 (1H, m), 2.24(1H, m), 3.21(3H, s) |
| 3 | (±)-3-n-butyl-3,4-diazabicyclo[4.1.0]heptane-2,5-dione | 104–105 | 0.94(3H, t, J=7.3Hz), 1.16(1H, m) 1.34(2H, m), 1.61 (2H, m), 1.70 (1H, m), 2.11(1H, m), 2.23(1H, m) 3.49(1H, m), 3.75(1H, m) |
| 4 | (±)-3-allyl-3,4-diazabicyclo[4.1.0]heptane-2,5-dione | 147–148 | 1.24(1H, q, J=5.0Hz), 1.73(1H, m) 2.16(1H, m), 2.26(1H, m), 4.22 (2H, m), 5.36–5.40(2H, m), 5.76 (1H, m) |
| 5 | (±)-3-(2-propyn-1-yl)-3,4-diazabicyclo[4.1.0]heptane-2,5-dione | 147–149 | 1.29(1H, m), 1.76(1H, m), 2.20 (1H, m), 2.26(1H, m), 2.37(1H, t, J=2.4Hz), 4.43(2H, d, J=2.4Hz), 9.61(1H, br s) |
| 6 | (±)-3-(2-methoxyethyl)-3,4-diazabicyclo[4.1.0]heptane-2,5-dione | 79–82 | 1.25 (1H, m), 1.70(1H, m), 2.12– 2.25 (2H, m), 3.39(3H, s), 3.57– 3.67 (2H, m), 3.74(1H, m), 3.92 (1H, m), 8.45(1H, br s) |
| 7 | (±)-3-(2-hydroxyethyl)-3,4-diazabicyclo[4.1.0]heptane-2,5-dione | 164–165 | (DMSO-d$_6$, TMS)1.06(1H, m), 1.59 (1H, m), 1.97–2.07(2H, m), 3.33– 3.71(4H, m), 4.80(1H, br s), 10.18(1H, br s) |
| 8 | (±)-3-phenethyl-3,4-diazabicyclo[4.1.0]heptane-2,5-dione | 160–162 | 0.95(1H, m), 1.50–1.65(1H, m), 2.07–2.13(1H, m), 2.16–2.22(1H, m), 2.89–3.01(2H, m), 3.65–3.73 (1H, m), 3.99–4.07(1H, m), 7.20– 7.32(5H, m), 10.39(1H, br s) |
| 9 | (±)-3-(2,2-diethoxyethyl)-3,4-diazabicyclo[4.1.0]heptane-2,5-dione | 83–84 | 1.20–1.30(7H, m), 1.70(1H, m), 2.10–2.30(2H, m), 3.50–3.64(3H, m), 3.18–3.82(2H, m), 3.91(1H, dd, J=14.7, 3.9Hz), 4.59(1H, dd, J=5.9, 3.9Hz), 8.16(1H, s) |
| 10 | (±)-3-(2-chlorobenzyl)-3,4-diazabicyclo[4.1.0]heptane-2,5-dione | | 1.18–1.23(1H, m), 1.65–1.71(1H, m, 2.06–2.11(1H, m), 2.24–2.29 (1H, m), 4.69(1H, d, J=16.1Hz), 5.04(1H, d, J=16.1Hz), 7.22–7.28 (4H, m), 7.36(1H, m) |
| 11 | (±)-3-(3-chlorobenzyl)-3,4-diazabicyclo[4.1.0]heptane-2,5-dione | 132–133 | 1.14–1.18(1H, m), 1.70–1.76(1H, m), 2.12–2.17(1H, m), 2.27–2.33 (1H, m), 4.67(1H, d, J=15.1Hz), 4.76(1H, d, J=15.1Hz), 7.07–7.35 (5H, m) |
| 12 | (±)-3-(4-chlorobenzyl)-3,4-diazabicyclo[4.1.0]heptane-2,5-dione | 187–188 | (DMSO-d$_6$, TMS)0.96–0.99(1H, m), 1.60–1.65(1H, m), 2.01–2.06(1H, m), 2.10–2.15(1H, m), 4.56(1H, d, J=15.6Hz), 4.67(1H, d, J=15.6Hz) 7.25(2H, d, J=8.3Hz), 7.40(2H, d J=8.3Hz), 10.50(1H, br s) |
| 13 | (±)-3-(2,6-dichlorobenzyl)-3,4-diazabicyclo[4.1.0]heptane-2,5-dione | 172–174 | 1.23–1.27(1H, m), 1.65–1.71 (1H, m), 2.11–2.17(1H, m), 2.25–2.31(1H, m), 4.82(1H, d, J=15.1Hz), 5.43(1H, d, J= 15.1Hz), 7.25–7.29(1H, m), 7.36–7.38(2H, m) |
| 14 | (±)-3-(2,4-dichlorobenzyl)-3,4-diazabicyclo[4.1.0]heptane-2,5-dione | 199–202 | (DMSO-d$_6$, TMS)1.14(1H, m) 1.64–1.70(1H, m), 2.07–2.18 (2H, m), 4.58(1H, d, J=16.6Hz), 4.78(1H, d, J=16.6Hz), 7.16 (1H, d, J=8.3Hz), 7.42(1H, dd, J=8.3, 2.0Hz), 7.63(1H, d, J= 2.0Hz), 10.57(1H, br s) |
| 15 | (±)-3-(2-fluorobenzyl)-3,4-diazabicyclo[4.1.0]heptane-2,5-dione | 138–140 | 1.15(1H, m), 1.65–1.71(1H, m), 2.07–2.12(1H, m), 2.23–2.29 (1H, m), 4.67(1H, d, J=15.6Hz), 4.98(1H, d, J=15.6Hz), 7.03– 7.14(2H, m), 7.26–7.33(2H, m), |

TABLE 1-continued

| Reference Example No. | Compound | Melting Point (°C.) | NMR Data (CDCl₃, TMS), δ (ppm) |
|---|---|---|---|
| 16 | (±)-3-(4-fluorobenzyl)-3,4-diazabicyclo[4.1.0]heptane-2,5-dione | 173–176 | 9.28(1H, br s) (DMSO-d₆, TMS)0.93–0.97(1H, m), 1.59–1.65(1H, m), 2.00–2.05(1H, m), 2.09–2.14(1H, m), 4.55(1H, d, J=15.6Hz), 4.66(1H, d, J=15.6Hz), 7.13–7.19(2H, m), 7.26–7.30(2H, m), 10.47(1H, br s) |
| 17 | (±)-3-(2-methylbenzyl)-3,4-diazabicyclo[4.1.0]heptane-2,5-dione | 177–190 | (DMSO-d₆, TMS)1.08(1H, m), 1.67(1H, m), 2.05–2.12(1H, m), 2.12–2.19(1H, m), 2.23(3H, s), 4.53(1H, d, J=16.6Hz),4.73(1H, d, J=16.6Hz), 6.90–7.00(1H, m), 7.10–7.20(3H, m), 10.34(1H, br s) |
| 18 | (±)-3-(4-methylbenzyl)-3,4-diazabicyclo[4.1.0]heptane-2,5-dione | 203–209 | (DMSO-d₆, TMS)0.93(1H, m), 1.61(1H, m), 1.98–2.04(1H, m), 2.08–2.13(1H, m), 2.27(3H, s), 4.51(1H, d, J=15.6Hz), 4.65(1H, d, J=15.6Hz), 7.11(2H, d, J=8.8Hz), 7.14(2H, d, J=8.8Hz), 10.37(1H, br s) |
| 19 | (±)-3-(4-methoxybenzyl)-3,4-diazabicyclo[4.1.0]heptane-2,5-dione | 180–183 | (DMSO-d₆, TMS)0.91(1H, m), 1.61(1H, m), 1.97–2.03(1H, m), 2.08–2.13(1H, m), 3.73(3H, s), 4.48(1H, d, J=15.1Hz), 4.61(1H, d, J=15.1Hz), 6.90(2H, d, J=8.3Hz), 7.18(2H, d, J=8.3Hz), 10.35(1H, br s) |
| 20 | (±)-3-(3,5-di-t-butyl-4-hydroxybenzyl)-3,4-diazabicyclo[4.1.0]heptane-2,5-dione ethanolate | 227–228 | 1.15(1H, m), 1.24(3H, t, J=6.8Hz) 1.42(18H, s), 1.69(1H, m), 2.11(1H, m), 2.28(1H, m), 3.72(2H, q, J=6.0Hz), 4.58(1H, d, J=15.1Hz), 4.75(1H, d, J=15.1Hz), 5.25(1H, br s), 7.14(2H, s), 9.45(1H, br s) |
| 21 | (±)-3-(3,5-dimethyl-4-hydroxybenzyl)-3,4-diazabicyclo[4.1.0]-heptane-2,5-dione | 200–202 | 1.23(1H, m), 1.71(1H, m), 2.15(1H, m), 2.22(6H, s), 2.28(1H, m), 4.51(1H, d, J=14.7Hz), 4.73(1H, d, J=14.7Hz), 4.80(1H, br s), 6.90(2H, s), 7.52(1H, br s) |
| 22 | (±)-3-(4-sulfamoylbenzyl)-3,4-diazabicyclo[4.1.0]heptane-2,5-dione | 250–253 | (DMSO-d₆, TMS)1.04(1H, m), 1.64(1H, m), 2.05(1H, m), 2.15(1H, m), 4.64(1H, d, J=16.1Hz), 4.76(1H, d, J,=16.1Hz), 7.33(2H, s), 7.39(2H, d, J=8.3Hz), 7.79(2H, d, J=8.3Hz), 10.54(1H, br s) |
| 23 | (±)-3-(2-methyl-2-propen-1-yl)-3,4-diazabicyclo[4.1.0]heptane-215-dione | 140–142 | 1.22(1H, m), 1.72(3H, s), 1.65-1.83(1H, m), 2.15(1H, m), 2.29(1H, m), 4.11(1H, d, J=15.6Hz), 4.25(1H, d, J=15.6Hz), 4.98(1H, s), 5.04(1H, s), 8.98(1H, br s) |
| 24 | (±)-3-(3-methyl-2-buten-1-yl)-3,4-diazabicyclo[4.1.0]heptane-2,5-dione | 99–101 | 1.20(1H, m), 1.69(1H, m), 1.74(3H, s), 1.78(3H, s), 2.13(1H m), 2.23(1H, m), 4.21(2H, d, J=7.3Hz), 5.15(1H, t, J=7.3Hz), 8.55(1H, br s) |

REFERENCE EXAMPLE 25

(±)-3,7,7-Trimethyl-3,4-diazabicyclo[4.1.0]heptane-2,5-dione

In 5 ml of ethyl alcohol were added 949 mg (6.77 mmol) of 3,3-dimethyl-1,2-cyclopropanedicarboxylic acid anhydride and 0.36 ml (6.77 mmol) of methylhydrazine, and the mixture was heated under reflux for 16 hours. The solvent was removed by distillation under reduced pressure, and the residue was purified by silica gel column chromatography. Recrystallization from ethyl acetate/hexane afforded 312 mg (27.3%) of the titled compound.

Melting Point: 151°–154° C.

NMR (CDCl₃, TMS) δ(ppm): 1.21 (3H, s), 1.34 (3H, s), 1.98 (1H, d, J=7.3 Hz), 2.10 (1H, d, J=7.3 Hz), 3.24 (3H, s)

REFERENCE EXAMPLE 26

(±)-3-(4-Hydroxybenzyl)-3,4-diazabicyclo[4.1.0]heptane-2,5-dione

To 5 ml of methylene chloride was added 462 mg (1.87 mmol) of (±)-3-(4-methoxybenzyl)-3,4-diazabicyclo[4.1.0]heptane-2,5-dione obtained in Reference Example 19. The mixture was cooled on a dry ice/ethanol bath, and 0.1 ml (1.1 mmol) of boron tribromide was added thereto dropwise. The temperature was elevated to room temperature, and the mixture was stirred for 2 hours. Water was added to the reaction mixture, and the mixture was extracted with ethyl acetate. The organic layer was dried over anhydrous sodium sulfate, the solvent was removed by distillation under reduced pressure, and the residue was recrystallized from ethanol/chloroform to obtain 120 mg (29.6%) of the titled compound.

NMR (DMSO-d$_6$, TMS) δ(ppm): 0.87–0.91 (1H, m), 1.56–1.62 (1H, m), 1.97–2.02 (1H, m), 2.07–2.12 (1H, m), 4.43 (1H, d, J=15.1 Hz), 4.57 (1H, d, J=15.1 Hz), 6.71 (2H, d, J=8.3 Hz), 7.05 (2H, d, J=8.3 Hz), 9.01 (1H, br s)

REFERENCE EXAMPLE 27

(±)-3-Isobutyl-3,4-diazabicyclo[4.1.0]heptane-2,5-dione

To 40 ml of ethyl alcohol was added 2.03 g (11.28 mmol) of (±)-3-(2-methyl-2-propen-1-yl)-3,4-diazabicyclo[4.1.0]heptane-2,5-dione obtained in Reference Example 23, and 230 mg of a 5% (w/w) palladium-on-carbon catalyst was added thereto to conduct catalytic reduction under normal pressure. After completion of the reaction, the catalyst was removed by filtration, the filtrate was concentrated under reduced pressure, and the residue was crystallized from ethyl acetate/hexane to obtain 1.6 g (80%) of the titled compound.

Melting Point: 150°–152° C.

NMR (CDCl$_3$, TMS) δ(ppm): 0.91 (3H, d, J=6.4 Hz), 0.95 (3H, d, J=6.8 Hz), 1.17 (1H, m), 1.71 (1H, m), 2.05 (1H, m), 2.13 (1H, m), 2.25 (1H, m), 3.23 (1H, dd, J=6.8, 14.2 Hz), 3.68 (1H, dd, J=7.8, 14.2 Hz), 10.14 (1H, br s)

REFERENCE EXAMPLE 28

(±)-3,4-Diazabicyclo[4.1.0]heptane-2,5-dione

In 1 l of methyl alcohol was dissolved 20.0 g (92.5 mmol) of (±)-3-benzyl-3,4-diazabicyclo[4.1.0]heptane-2,5-dione obtained in Reference Example 1, and 29.2 g (462 mmol) of ammonium formate and 29.2 g of a 10% (w/w) palladium-on-carbon catalyst were added thereto, followed by heating under reflux for 2 hours. The catalyst was removed by filtration, and the solvent was removed by distillation under reduced pressure to yield 12.33 g (100%) of the titled compound.

Melting Point: 193°–195° C.

NMR (DMSO-d$_6$, TMS) δ(ppm): 0.99 (1H, m), 1.58 (1H, m), 1.91 (2H, m), 10.05 (2H, br s)

REFERENCE EXAMPLE 29

(±)-2-Amino-4-methyl-3,4-diazabicyclo[4.1.0]hept-2-en-5-one

In 25 ml of benzene was dissolved 13.77 g (97 mmol) of chlorosulfonyl isocyanate, and to the solution was added 12.7 g (88 mmol) of cis-methyl hydrogen cyclopropane-1,2-dicarboxylate which had been synthesized by the process of Journal of Organic Chemistry, Vol. 36, pp. 3356–3361 (1971). The mixture was stirred on an oil bath at 60° C. for 30 minutes. After cooling, 13.6 ml (176 mmol) of DMF was added thereto, followed by stirring for 30 minutes. Water was added thereto, and the reaction mixture was extracted with benzene. The organic layer was washed successively with water and a saturated sodium chloride aqueous solution, and dried over anhydrous sodium sulfate. The solvent was removed by distillation under reduced pressure, and the residue was distilled under reduced pressure to obtain 6.14 g (55.7%) of methyl cis-2-cyanocyclopropanecarboxylate.

Boiling Point: 94°–98° C./4 mmHg

NMR (CDCl$_3$, TMS) δ(ppm): 1.43 (1H, m), 1.69 (1H, m), 1.86 (1H, m), 2.15 (1H, m), 3.80 (3H, s)

In 150 ml of methyl alcohol was dissolved 2.2 g (96 mmol) of sodium, and to the solution were added a solution of 6.01 g (48 mol) of the above-prepared compound in 5 ml of methyl alcohol and a solution of 2.21 g (48 mmol) of methylhydrazine in 5 ml of methyl alcohol, followed by stirring at room temperature for 67 hours. The reaction mixture was concentrated under reduced pressure, and the concentrate was purified by silica gel column chromatography. Recrystallization from ethyl alcohol furnished 557 mg (8.6%) of the titled compound.

Melting Point: 197°–200° C.

NMR (CDCl$_3$, TMS) δ(ppm): 0.84 (1H, m), 1.54 (1H, m), 1.97 (1H, m), 2.17 (1H, m), 3.18 (3H, s), 4.18 (2H, br s)

REFERENCE EXAMPLE 30

3,4-Dihydro-2,2-dimethyl-3,4-epoxy-2H-1-benzohyran-6,7-dicarboxyimide

1) Dimethyl 3,4-Dihydro-2,2-dimethyl-4-oxo-2H-1-benzopyran-6,7-dicarboxylate:

In 100 ml of acetone was dissolved 4.2 g of dimethyl 4-acetyl-5-hydroxyphthalate synthesized in accordance with the process of Bulletin of the Chemical Society of Japan, Vol. 57, p. 3221 (1984). To the solution were added 1.0 ml of pyrrolidine and a small amount of Molecular Sieve (3A), followed by stirring at room temperature for 3 days. Any insoluble material was removed by filtration, and the solvent was removed by distillation under reduced pressure. The residue was purified by silica gel column chromatography to obtain 4.6 g (86.3%) of a yellow oily substance.

NMR (CDCl$_3$, TMS) δ(ppm): 1.48 (6H, s), 2.77 (2H, s), 3.88 (3H, s), 3.93 (3H, s), 7.09 (1H, s), 8.41 (1H, s)

2) Dimethyl 3,4-Dihydro-2,2-dimethyl-4-hydroxy-2H-1-benzopyran-6,7-dicarboxylate:

In 4 ml of methyl alcohol was dissolved 0.15 g (0.51 mmol) of the compound obtained in (1) above, and 23 mg of sodium borohydride was added thereto under cooling with ice, followed by stirring at the same temperature for 10 minutes. The reaction mixture was poured into water, made weakly acidic with diluted hydrochloric acid, and extracted with chloroform. The extract was dried over anhydrous sodium sulfate, and the solvent was removed by distillation under reduced pressure to obtain 0.141 g (93.8%) of a pale yellow oily substance.

NMR (CDCl$_3$, TMS) δ(ppm): 1.30 (3H, s), 1.45 (3H, s), 1.86 (1H, dd, J=9.5, 13.4 Hz), 2.19 (1H, dd, J=6.4, 13.4 Hz), 3.85 (3H, s), 3.88 (3H, s), 4.83 (1H, dd, J=6.4, 9.5 Hz), 6.96 (1H, s), 7.99 (1H, s)

3) Dimethyl 2,2-Dimethyl-2H-1-benzopyran-6,7-dicarboxylate:

In 5 ml of benzene was dissolved 0.14 g (0.475 mmol) of the compound obtained in (2) above, and 10 mg of p-toluenesulfonic acid was added thereto, followed by heating under reflux for 1 hour. After allowing to cool, ethyl acetate was added thereto, and the reaction mixture was washed successively with a saturated sodium hydrogencarbonate aqueous solution and a saturated sodium chloride aqueous solution and dried over anhydrous sodium sulfate. Removal of the solvent by distillation gave 0.123 g (93.5%) of a pale yellow oily substance.

NMR (CDCl3, TMS) δ(ppm): 1.44 (6H, s), 3.85 (3H, s), 3.88 (3H, s), 5.71 (1H, d, J=9.8 Hz), 6.32 (1H, d, J=9.8 Hz), 6.96 (1H, s), 7.45 (1H, s)

4) 2,2-Dimethyl-2H-1-benzopyran-6,7-dicarboxylic Acid Anhydride

In 10 ml of ethyl alcohol was dissolved 2.0 g (7.2 mmol) of the compound obtained in (3) above, and 10 ml (20 mmol) of a 2N sodium hydroxide aqueous solution was added thereto, followed by stirring at room temperature for 1.5 hours. Ethyl alcohol was removed by distillation under reduced pressure, and the residue was made acidic with 50 ml of 10% (w/w) hydrochloric acid, and extracted with diethyl ether. The diethyl ether layer was dried over anhydrous sodium sulfate, and the solvent was removed by distillation under reduced pressure to obtain 2.2 g of a brown oily substance, which was then dissolved in 10 ml of acetic anhydride, and the solution was heated under reflux for 7.5 hours. After allowing to cool, the solvent was removed by distillation under reduced pressure to obtain 1.62 g (79.4%) of a yellow solid.

NMR (CDCl3, TMS) δ(ppm): 1.51 (6H, s), 5.90 (1H, d, J=10.2 Hz), 6.43 (1H, d, J=10.2 Hz), 7.26 (1H, s), 7.54 (1H, s)

5) 2,2-Dimethyl-2H-1-benzopyran-6,7-dicarboxyimide

To a solution of 0.50 g (2.17 mmol) of the compound obtained in (4) above in 10 ml of dioxane was added 5 ml of concentrated aqueous ammonia, followed by heating under reflux for 7.5 hours. After allowing to cool, the solvent was removed by distillation, and the residue was purified by silica gel column chromatography to obtain 0.23 g (46%) of white crystals.

Melting Point: 201°–202° C.

NMR (CDCl3, TMS) δ(ppm): 1.48 (6H, s), 5.79 (1H, d, J=9.9 Hz), 6.40 (1H, d, J=9.9 Hz), 7.17 (1H, s), 7.43 (1H, s)

6) 3,4-Trans-3-bromo-3,4-dihydro-2,2-dimethyl-4-hydroxy-2H-1-benzopyran-6,7-dicarboxyimide:

In a mixed solvent of 3 ml of dimethyl sulfoxide and 0.1 ml of water was dissolved 99.6 mg (0.43 mmol) of the compound obtained in (5) above, and 150 mg (0.84 mmol) of N-bromosuccinimide was added thereto, followed by stirring at room temperature for 4 days. The reaction mixture was poured into water and extracted with ethyl acetate. The extract was washed with water and then with diluted hydrochloric acid and dried over anhydrous sodium sulfate. The solvent was removed by distillation under reduced pressure, and the residue was washed with chloroform and filtered to give 0.114 g (80.5%) of white crystals.

Melting Point: 230°–232° C.

NMR (DMSO-d6, TMS) δ(ppm): 1.42 (3H, s), 1.58 (3H, s), 4.34 (1H, d, J=8.3 Hz), 4.88 (1H, dd, J=8.3, 6.8 Hz), 6.50 (1H, d, J=6.8 Hz), 7.13 (1H, s), 7.83 (1H, s)

7) 3,4-Dihydro-2,2-dimethyl-3,4-epoxy-2H-1-benzopyran-6,7-dicarboxyimide

In 20 ml of DMF was dissolved 1.02 g (3.13 mmol) of the compound obtained in (6) above, and 0.27 g (6.75 mmol) of 60% (w/w) (oily) sodium hydride was added thereto, followed by stirring at room temperature for 2 hours. The reaction mixture was poured into a mixture of a saturated ammonium chloride aqueous solution and ethyl acetate, followed by stirring. The organic layer was separated. The aqueous layer was extracted with ethyl acetate. The combined organic extracts were dried, the solvent was removed by distillation under reduced pressure, and the residue was washed with hexane to give 0.62 g (80.8%) of the titled compound.

NMR (CDCl3, TMS) δ(ppm): 1.32 (3H, s), 1.63 (3H, s), 3.59 (1H, d, J=4.4 Hz), 4.02 (1H, d, J=4.4 Hz), 7.24 (1H, s), 7.86 (1H, s)

The compound obtained in each of Examples 1 to 19 hereinafter described was a racemate composed of a compound (Ip) shown below wherein the configuration at the 3-, 4-, 1'- and 6'-positions is S, R, S, and R, respectively, and its optical antipode, or a racemate composed of the compound shown wherein the configuration at the 3-, 4-, 1'- and 6'-positions is S, R, R, and S, respectively, and its optical antipode. The compound obtained in each of Examples 21 to 57 hereinafter described was an optically active compound (Ip) wherein the configuration at the 3-, 4-, 1'- and 6'-positions is S, R, S, and R, respectively, or S, R, R, and S, respectively.

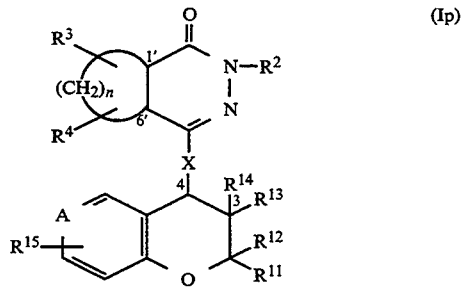

wherein $R^2$, $R^3$, $R^4$, $R^{11}$, $R^{12}$, $R^{13}$, $R^{14}$, $R^{15}$, A, n, and X are as defined above.

EXAMPLE 1

3,4-trans-4-(3-Benzyl-2-oxo-3,4-diazabicyclo[4.1.0]hept-4-en-5-yloxy)-3,4-dihydro-2,2-dimethyl-3-hydroxy-2H-1-benzopyran-6-carbonitrile In 100 ml of ethyl alcohol were added 3.00 g (13.8 mmol) of (±)-3-benzyl-3,4-diazabicyclo[4.1.0]heptane-2,5-dione obtained in Reference Example 1, 2.79 g (13.8 mmol) of (±)-3,4-dihydro-2,2-dimethyl-3,4-epoxy-2H-1-benzopyran-6-carbonitrile, and 1.1 ml (13.8 mmol) of pyridine, and the mixture was heated under reflux for 16 hours. The solvent was removed by distillation under reduced pressure, and to the residue was added ethyl alcohol. Recrystallization of the insoluble crude crystals from methyl alcohol yielded 1.41 g (24.3%) of the titled compound.

Melting Point: 242°–245° C. (decomposition)

Rf Value=0.50 (silica gel thin layer chromatography (TLC); developing solvent: chloroform/methyl alcohol=20:1, v/v)

NMR (CDCl$_3$, TMS) δ(ppm): 1.01 (1H, m), 1.25 (3H, s), 1.44 (3H, s), 1.73 (1H, m), 2.18 (1H, m), 2.33 (1H, m), 3.00 (1H, d, J=4.3 Hz), 3.76 (1H, dd, J=4.3, 7.3 Hz), 4.75 (1H, d, J=14.4HZ), 4.85 (1H, d, J=14.4 Hz), 5.60 (1H, d, J=7.8 Hz), 6.88 (1H, d, J=8.3 Hz), 7.30 (5H, m), 7.48 (1H, dd, J=2.0, 8.3 Hz), 7.52 (1H, s)

EXAMPLES 2 TO 8

Compounds shown in Table 2 below were synthesized in the same manner as in Example 1. The melting point (m.p.), Rf value in silica gel TLC, and NMR data of the compounds are also shown. The NMR spectra were run in CDCl$_3$, except where noted. In Table 2, EtOAc means ethyl acetate, and MeOH means methyl alcohol (hereinafter the same).

TABLE 2

| Example No. | Compound | m.p. (°C.) | Rf Value (Developing Solvent) | NMR Data (CDCl$_3$, TMS)δ (ppm) |
|---|---|---|---|---|
| 2 | 3,4-trans-3,4-dihydro-2,2-dimethyl-3-hydroxy-4-(3-methyl-2-oxo-3,4-diazabicyclo[4.1.0]hept-4-en-5-yloxy)-2H-1-benzopyran-6-carbonitrile | 190–191 | 0.33 (EtOAc) | 1.03(1H, m), 1.33(3H, s), 1.53(3H, s), 1.73(1H, m), 2.20(1H, m), 2.25(1H, m), 3.24(3H, s), 3.93(1H, d, J=7.8Hz), 4.21(1H, br s), 5.73 (1H, d, J=7.8Hz), 6.91(1H, d, J=8.5Hz), 7.51(1H, dd, J=2.0, 8.5Hz), 7.61(1H, d, J=2.0Hz) |
| 3 | 3,4-trans-4-(3-n-butyl-2-oxo-3,4-diazabicyclo[4.1.0]hept-4-en-5-yloxy)-3,4-dihydro-2,2-dimethyl-3-hydroxy-2H-1-benzopyran-6-carbonitrile | 169–170 | 0.37 (EtOAc) | 0.93(3H, t, J=7.3Hz), 0.95 (1H, m), 1.33(3H, s), 1.33 (2H, m), 1.53(3H, s), 1.59 (2H, m), 1.72(1H, m), 2.20 (1H, m), 2.27(1H, m), 3.48 (1H, m), 3.77(1H, m), 3.93 (1H, dd, J=2.0, 7.8Hz), 3.95 (1H, d, J=2.0Hz), 5.70(1H, d, J=7.8Hz), 6.91(1H, d, J=8.3Hz), 7.51(1H, dd, J=2.0, 8.3Hz), 7.64(1H, d, J=2.0Hz) |
| 4 | 3,4-trans-4-(3-allyl-2-oxo-3,4-diazabicyclo[4.1.0]hept-4-en-5-yloxy)-3,4-dihydro-2,2-dimethyl-3-hydroxy-2H-1-benzopyran-6-carbonitrile | 181–182 | 0.42 (CHCl$_3$/MeOH = 10:1, v/v) | 1.04(1H, m), 1.30(3H, s), 1.51(3H, s), 1.74(1H, m), 2.21(1H, m), 2.30(1H, m), 3.79(1H, br s), 3.90(1H, d, J=7.3Hz), 4.15(1H, dd, J=6.3, 14.6Hz), 4.32(1H, dd, J=5.9, 14.6Hz), 5.20–5.26(2H, m), 5.70(1H, d, J=7.7Hz), 5.83 (1H, m), 6.90(1H, d, J=8.3Hz) 7.50(1H, dd, J=2.0, 8.3Hz), 7.65(1H, d, J=2.0Hz) |
| 5 | 3,4-trans-3,4-dihydro-2,2-dimethyl-4-(3-methyl-2-oxo-3,4-diazabicyclo-[4.1.0]hept-4-en-5-yloxy)-6-nitro-2H-1-benzopyran-3-ol | 219–223 | 0.25 (CHCl$_3$/MeOH = 20:1, v/v) | (DMSO-d$_6$, TMS)0.86–0.90(1H, m) 1.31(3H, s), 1.44(3H, s), 1.65–1.70(1H, m), 2.17–2.25 (2H, m), 3.15(3H, s), 3.86(1H, dd, J=5.4, 6.4Hz), 5.73(1H, d, J=6.4Hz), 5.98(1H, d, J=5.4Hz), 7.03(1H, d, J=8.8Hz), 8.11(1H, dd, J=2.9, 8.8Hz), 8.20(1H, d, J=2.9Hz) |
| 6 | 3,4-trans-3,4-dihydro-2,2-dimethyl-3-hydroxy-4-(3-(2-hydroxyethyl)-2-oxo-3,4-diazabicyclo[4.1.0]hept-4-en-5-yloxy)-2H-1-benzopyran-6-carbonitrile | 152–153 | 0.14 (EtOAc) | 1.08(1H, m), 1.33(3H, s), 1.51 (3H, s), 1.76(1H, m), 2.23(1H, m), 2.31(1H, m), 2.80(1H, t, J=5.3Hz), 3.63(1H, m), 3.87(2H m), 3.92(1H, dd, J=4.4, 7.3Hz), 4.04(1H, m), 4.06(1H, d, J=4.4Hz), 5.80(1H, d, J=7.3Hz), 6.91(1H, d, J=8.3Hz), 7.50(1H, dd, J=2.0, 8.3Hz), 7.62(1H, d, J=2.0Hz) |
| 7 | 3,4-trans-4-(3-(4-chlorobenzyl)-2-oxo-3,4-diazabicyclo[4.1.0]-hept-4-en-5-yloxy)-3,4-dihydro-2,2-dimethyl-3-hydroxy-2H-1-benzopyran-6-carbonitrile | 200–202 | 0.40 (CHCl$_3$/MeOH = 20:1, v/v) | 0.94–0.98(1H, m), 1.30(3H, s), 1.52(3H, s), 1.54–1.63(1H, m), 1.92–1.95(1H, m), 2.04–2.10 (1H, m), 3.86(1H, dd, J=3.9, 7.8Hz), 4.11(1H, br s), 4.59 (1H, d, J=14.1Hz), 4.80(1H, d, J=14.1Hz), 5.71(1H, d, J=7.8 Hz), 6.89(1H, d, J=8.3Hz), 7.28(4H, m), 7.49(1H, dd, J= 8.3, 1.9Hz), 7.50(1H, s) |
| 8 | 3,4-trans-3,4-dihydro-2,2-dimethyl-3-hydroxy-4-(2-oxo-3,7,7-trimethyl-3,4-diazabicyclo[4.1.0]hept-4-en-5-yloxy)-2H-1-benzopyran-6-carbonitrile | 190–197 | 0.39 (EtOAc) | 1.14(3H, s), 1.34(3H, s), 1.37 (3H, s), 1.53(3H, s), 2.04(1H, d, J=7.3Hz), 2.14(1H, d, J= 7.3Hz), 3.29(3H, s), 3.80(1H, d, J=2.9Hz), 3.92(1H, dd, J= 2.9, 7.8Hz), 5.76(1H, d, J= 7.8Hz), 6.91(1H, d, J=8.3Hz), 7.50(1H, dd, J=2.0, 8.3Hz), |

| Example No. | Compound | m.p. (°C.) | Rf Value (Developing Solvent) | NMR Data (CDCl$_3$, TMS)δ (ppm) |
|---|---|---|---|---|
| | | | | 7.52(1H, d, J=2.0Hz) |

EXAMPLE 9

3,4-trans-3,4-Dihydro-2,2-dimethyl-4-(3-methyl-2-oxo-3,4-diazabicyclo[4.1.0]hept-4-en-5-yloxy)-6-trifluoromethoxy-2H-1-benzopyran-3-ol In 20 ml of ethyl alcohol was dissolved 1.0 g (3.84 mmol) of (±)-3,4-dihydro-2,2-dimethyl-3,4-epoxy-6-trifluoromethoxy-2H-1-benzopyran which had been synthesized according to the process of JP-B-1-151571 (the term "JP-B" as used herein means an "examined published Japanese patent application"), and to the solution were added 0.6 g (4.28 mmol)of (±)-3-methyl-3,4-diazabicyclo[4.1.0]heptane-2,5-dione and 0.35 ml (4.34 mmol) of pyridine. The mixture was heated under reflux for 16 hours. The solvent was removed by distillation under reduced pressure. The residue was purified by silica gel column chromatography and recrystallized from ethyl acetate/hexane to obtain 0.32 g (20.6%) of the titled compound.

Melting Point: 189°–190° C.
Rf Value: 0.33 (CHCl$_3$/MeOH=20:1, v/v)
NMR (CDCl$_3$, TMS) δ(ppm): 0.99 (1H, m), 1.32 (3H, s), 1.51 (3H, s), 1.68 (1H, m), 2.15–2.30 (2H, m), 3.25 (3H, s), 3.90–3.96 (2H, m), 5.71 (1H, d, J=7.3 Hz), 6.85 (1H, d, J=9.3 Hz), 7.10 (1H, d, J=9.3 Hz), 7.15 (1H, s)

EXAMPLE 10

3,4-trans-3,4-Dihydro-2,2-dimethyl-4-(3-methyl-2-oxo-3,4-diazabicyclo[4.1.0]hept-4-en-5-yloxy)-6-phenylsulfonyl-2H-1-benzopyran-3-ol In 15 ml of ethyl alcohol were suspended 0.96 g (3.03 mmol) of (±)-3,4-dihydro-2,2-dimethyl-3,4-epoxy-6-phenylsulfonyl-2H-1-benzopyran which had been synthesized according to the process of JP-B-1-287083 and 0.81 g (5.78 mmol)of (±)-3-methyl-3,4-diazabicyclo[4.1.0]heptane-2,5-dione, and to the suspension was added 0.3 ml (3.9 mmol) of pyridine. The mixture was heated under reflux for 6 hours. The solvent was removed by distillation under reduced pressure. The residue was purified by silica gel column chromatography. Recrystallization from ethyl acetate/hexane gave 0.181 g (13%) of the titled compound.

Melting Point: 118°–121° C.
Rf Value: 0.24 (CHCl$_3$/MeOH=20:1, v/v)
NMR (CDCl$_3$, TMS) δ(ppm): 0.99 (1H, m), 1.32 (3H, s), 1.51 (3H, s), 1.66–1.72 (1H, m), 2.14–2.26 (2H, m), 3.23 (3H, s), 3.92 (1H, dd, J=3.4, 7.3 Hz), 4.23 (1H, br s), 5.76 (1H, d, J=7.3 Hz), 6.91 (1H, d, J=8.8 Hz), 7.48–7.58 (3H, m), 7.74 (1H, dd, J=2.4, 8.8 Hz), 7.88–7.94 (3H, m)

EXAMPLE 11

3,4-trans-3,4-Dihydro-2,2-dimethyl-3-hydroxy-4-(3-methyl-2-oxo-3,4-diazabicyclo[4.1.0]-hept-4-en-5-yloxy]-2H-1-benzopyran-6-sulfonamide To 20 ml of DMF was added 2.5 g (7.44 mmol) of trans-3-bromo-3,4-dihydro-2,2-dimethyl-4-hydroxy-2H-1-benzopyran-6-sulfonamide which had been synthesized according to the process of JP-B-2-300182, and 0.75 g (18.75 mmol) of 60% (w/w) sodium hydride was added thereto, followed by stirring at room temperature for 20 minutes. The reaction mixture was poured into a saturated ammonium chloride aqueous solution and adjusted to pH 5 with hydrochloric acid. The reaction mixture was extracted with ethyl acetate, the extract was washed with a saturated ammonium chloride aqueous solution, and the organic layer was dried over anhydrous sodium sulfate. Removal of the solvent by distillation under reduced pressure afforded 2.6 g of a pale brown oily substance. The oily substance was dissolved in 40 ml of ethyl alcohol, and 1.05 g (7.50 mmol)of (±)-3-methyl-3,4-diazabicyclo[4.1.0]heptane-2,5-dione and 1.0 ml (12.3 mmol) of pyridine were added thereto, followed by heating under reflux for 15 hours. The solvent was removed by distillation under reduced pressure, and the residue was purified by silica gel column chromatography and recrystallized from chloroform to yield 0.262 g (8.9%) of the titled compound.

Melting Point: 236°–238° C.
Rf Value: 0.40 (CHCl$_3$/MeOH=10:1, v/v)
NMR (DMSO-d$_6$, TMS) δ(ppm): 0.86–0.92 (1H, m), 1.27 (3H, s), 1.40 (3H, s), 1.62–1.67 (1H, m), 2.15–2.24 (2H, m), 3.13 (3H, s), 3.78 (1H, dd, J=5.4, 6.4 Hz), 5.73 (1H, d, J=6.4 Hz), 5.88 (1H, d, J=5.4 Hz), 6.95 (1H, d, J=8.3 Hz), 7.65 (1H, dd, J=8.3, 2.0 Hz), 7.72 (1H, d, J=2.0 Hz)

EXAMPLE 12

3,4-trans-3,4-Dihydro-2,2-dimethyl-3-hydroxy-4-(3-methyl-2-oxo-3,4-diazabicyclo[4.1.0]-hept-4-en-5-yloxy)-7-nitro-2H-1-benzopyran-6-acetamide To 20 ml of ethyl alcohol were added 556 mg (2.0 mmol) of (±)-3,4-dihydro-2,2-dimethyl-3,4-epoxy-7-nitro-2H-1-benzopyran-6-acetamide which had been synthesized according to the process of JP-B-59-1475, 280 mg (2.0 mmol) of (±)-3-methyl-3,4-diazabicyclo[4.1.0]heptane-2,5-dione, and 0.16 ml (2.0 mmol) of pyridine, and the mixture was heated under reflux for 16 hours. The solvent was removed by distillation under reduced pressure, and the residue was purified by silica gel column chromatography, followed by recrystallization from ethyl acetate to give 123 mg (14.7%) of the titled compound.

Melting Point: 239°–240° C.
Rf Value: 0.34 (CHCl$_3$/MeOH=20:1, v/v)
NMR (CDCl$_3$, TMS) δ(ppm): 1.17 (1H, m), 1.32 (3H, s), 1.56 (3H, s), 1.70 (1H, m), 2.21 (2H, m), 2.25 (3H, s), 3.25 (3H, s), 3.75 (1H, d, J=3.4 Hz), 3.96 (1H, dd, J=3.4, 7.8 Hz), 5.79 (1H, d, J=7.8 Hz), 7.68 (1H, s), 8.76 (1H, s), 10.00 (1H, br s)

EXAMPLE 13

3,4-trans-3,4-Dihydro-2,2-dimethyl-4-(3-methyl-2-oxo-3,4-diazabicyclo[4.1.0]hept-4-en-5-yloxy)-7-nitro-2H-1-benzopyran-3-ol To 20 ml of ethyl alcohol were added 442 mg (2.0 mmol) of (±)-3,4-dihydro-2,2-dimethyl-3,4-epoxy-7-nitro-2H-1-benzopyran which had been synthesized according to the process of J. Med. Chem., Vol. 26, pp. 1582–1589 (1983), 280 mg (2.0 mmol) of (±)-3-methyl- 3,4-diazabicyclo[4.1.0]heptane-2,5-dione, and 0.16 ml (2.0 mmol) of pyridine, and the mixture was heated under reflux for 16 hours. The solvent was removed by distillation under reduced pressure, and the residue was purified by silica gel column chromatography and recrystallized from ethyl alcohol to obtain 127 mg (17.5%) of the titled compound.

Melting Point: 236°–237° C.
Rf Value: 0.29 (ethyl acetate)
NMR (CDCl₃, TMS) δ(ppm): 1.00 (1H, m), 1.34 (3H, s), 1.54 (3H, s), 1.69 (1H, m), 2.21 (1H, m), 2.28 (1H, m), 3.25 (3H, s), 3.84 (1H, d, J=3.4 Hz), 3.97 (1H, dd, J=3.4, 7.3 Hz), 5.78 (1H, d, J=7.3 Hz), 7.45 (1H, d, J=8.3 Hz), 7.71 (1H, d, J=2.0 Hz), 7.78 (1H, dd, J=2.0, 8.3 Hz)

EXAMPLE 14

3,4-trans-3,4-Dihydro-3-hydroxy-4-(3-methyl-2-oxo-3,4-diazabicyclo[4.1.0]hept-4-en-5-yloxy)-2,2,3-trimethyl-2H-1-benzopyran-6-carbonitrile To 10 ml of ethyl alcohol were added 266 mg (1.23 mmol) of (±)-3,4-dihydro-3,4-epoxy-2,2,3-trimethyl-H-1-benzopyran-6-carbonitrile which had been synthesized according to the process of *J. Med. Chem.*, Vol. 34, pp. 3074–3085 (1991), 173 mg (1.23 mmol) of (±)-3-methyl-3,4-diazabicyclo[4.1.0]heptane-2,5-dione, and 0.1 ml (0.13 mmol) of pyridine, and the mixture was heated under reflux for 7 days. The solvent was removed by distillation under reduced pressure. The residue was purified by silica gel column chromatography. Recrystallization from ethyl acetate gave 125 mg (28.4%) of the titled compound.

Melting Point: 226°–227° C.
Rf Value: 0.21 (ethyl acetate)
NMR (CDCl₃, TMS) δ(ppm): 1.03 (1H, m). 1.24 (3H, s), 1.42 (3H, s), 1.50 (3H, s), 1.73 (1H, m), 2.22–2.31 (2H, m), 3.24 (3H, s), 3.95 (1H, s), 5.83 (1H, s), 6.90 (1H, d, J=8.3 Hz), 7.51 (1H, dd, J=2.0, 8.3 Hz), 7.65 (1H, d, J=2.0 Hz)

EXAMPLE 15

3,4-trans-3,4-Dihydro-3-hydroxy-4-(3-methyl-2-oxo-3,4-diazabicyclo[4.1.0]hept-4-en-5-yloxy)-2,2-tetramethylene-2H-1-benzopyran-6-carbonitrile ½ Hydrate The titled compound was prepared in the same manner as in Example 1, except for using (±)-3,4-dihydro-3,4-epoxy-2,2-tetramethylene-2H-1-benzopyran-6-carbonitrile synthesized according to the process of JP-B-1-294677.

Melting Point: 207°–210° C.
Rf Value: 0.30 (CHCl₃/MeOH=20:1, v/v)
NMR (CDCl₃, TMS) δ(ppm): 0.99–1.03 (1H, m), 1.64–1.98 (8H, m), 2.08–2.28 (3H, m), 3.24 (3H, s), 3.87 (1H, d, J=3.9 Hz), 4.13 (1H, dd, J=3.9, 6.8 Hz), 5.73 (1H, d, J=6.8 Hz), 6.91 (1H, d, J=8.3 Hz), 7.50 (1H, dd, J=8.3, 2.0 Hz), 7.62 (1H, d, J=2.0 Hz)

EXAMPLE 16

3,4-trans-3,4-Dihydro-2,2-dimethyl-4-(3-methyl-2-oxo-3,4-diazabicyclo[4.1.0]-hept-4-en-5-yloxy)-2H-pyrano[3,2-c]pyridin-3-ol The titled compound was prepared in the same manner as in Example 1, except for using (±)-3,4-dihydro-2,2-dimethyl-3,4-epoxy-2H-pyrano[3,2-c]pyridine synthesized according to the process of JP-B-61-293984, instead of (±)-3,4-dihydro-2,2-dimethyl-3,4-epoxy-2H-1-benzopyron-6-carbonitrile.

Rf Value: 0.46 (CHCl₃/MeOH=10:1, v/v)
NMR (CDCl₃, TMS) δ(ppm): 0.97–1.01 (1H, m), 1.32 (3H, s), 1.54 (3H, s), 1.67–1.73 (1H, m), 2.24–2.37 (2H, m), 3.26 (3H, s), 3.93 (1H, dd, J=2.0, 7.8 Hz), 4.82 (1H, d, J=2.0 Hz), 5.66 (1H, d, J=7.8 Hz), 6.77 (1H, d, J=5.4 Hz), 8.36 (1H, d, J=5.4 Hz), 8.50 (1H, s)

EXAMPLE 17

3,4-trans-4-(3-(2-Aminoethyl)-2-oxo-3,4-diazabicyclo[4.1.0]hept-4-en-5-yloxy)-3,4-dihydro-2,2-dimethyl-3-hydroxy-2H-1-benzopyran-6-carbonitrile To 10 ml of THF were added 303 mg (0.8 mmol) of 3,4-trans-3,4-dihydro-2,2-dimethyl-3-hydroxy-4-(3-(2-hydroxyethyl)-2-oxo-3,4-diazabicyclo[4.1.0]hept-4-en-5-yloxy)-2H-1-benzopyran-6-carbonitrile prepared in Example 6, 456 mg (1.6 mmol) of dibenzyl imidodicarboxylate, and 419 mg (1.6 mmol) of triphenylphosphine, and a solution of 278 mg (1.6 mmol) of diethyl azodicarboxylate in 2 ml of THF was added thereto dropwise. The mixture was stirred at room temperature for 2 hours. The solvent was removed by distillation under reduced pressure. The residue was purified by silica gel column chromatography and recrystallized from ethyl acetate/hexane to afford 312 mg (61.1%) of 3,4-trans-4-(3-(2-(N,N-bis(benzyloxycarbonyl))aminoethyl)-2-oxo-3,4-diazabicyclo[4.1.0]hept-4-en-5-yloxy)-3,4-dihydro-2,2-dimethyl-3-hydroxy-2H-1-benzopyran-6-carbonitrile.

Melting Point: 148°–149° C.
NMR (CDCl₃, TMS) δ(ppm): 0.91 (1H, m), 1.37 (3H, s), 1.47 (3H, s), 1.54 (1H, m), 1.91 (2H, m), 3.46 (1H, m), 3.79 (1H, dd, J=6.4, 6.8 Hz), 3.85 (1H, d, J=6.8 Hz), 3.91 (1H, m), 4.14 (1H, m). 4.26 (1H, m). 5.18 (2H, d, J=12.2 Hz), 5.25 (2H, d, J=12.2 Hz), 5.71 (1H, d, J=6.4 Hz), 6.90 (1H, d, J=8.8 Hz), 7.26 (10H, m), 7.44 (1H, d, J=2.0 Hz), 7.49 (1H, dd, J=2.0, 8.8 Hz)

In 20 ml of methyl alcohol was dissolved 291 mg (0.455 mmol) of the above obtained compound, and 30 mg of a 10% (w/w) palladium-on-carbon catalyst was added thereto to conduct hydrogenolysis under normal pressure. After completion of the reaction, the catalyst was removed by filtration, and the solvent was removed by distillation under reduced pressure to obtain 168 mg (100%) of the titled compound.

Rf Value: 0.15 (CHCl₃/MeOH=4:1, v/v)
NMR (CDCl₃, TMS) δ(ppm): 1.03 (1H, m), 1.32 (3H, s), 1.50 (3H, s), 1.73 (1H, m), 1.60–2.70 (3H), 2.21 (1H, m), 2.30 (1H, m), 3.00 (2H, m), 3.54 (1H, m), 3.88 (1H, d, J=7.3 Hz), 3.89 (1H, m), 5.82 (1H, d, J=7.3 Hz), 6.90 (1H, d, J=8.8 Hz), 7.50 (1H, dd, J=2.0, 8.8 Hz), 7.63 (1H, d, J=2.0 Hz)

EXAMPLE 18

3,4-trans-4-(3-(2-Acetamidoethyl)-2-oxo-3,4-diazabicyclo[4.1.0]hept-4-en-5-yloxy)-3,4-dihydro-2,2-dimethyl-3-hydroxy-2H-1-benzopyran-6-carbonitrile To 10 ml of methylene chloride was added 108 mg (0.29 mmol) of 3,4-trans-4-(3-(2-aminoethyl)-2-oxo-3,4-diazabicyclo[4.1.0]hept-5-en-5-yloxy)-3,4-dihydro-2,2-dimethyl-3-hydroxyl-2H-1-benzopyran-6-carbonitrile prepared in Example 17, and 0.04 ml (0.29 mmol) of triethylamine and a solution of 23 mg (0.29 mmol) of acetyl chloride in 2 ml of methylene chloride were added thereto, followed by stirring at room temperature for 2 hours. Removal of the solvent by distillation under reduced pressure, followed by purification by column chromatography on silica gel and recrystallization from ethyl acetate furnished 55 mg (45.8%) of the titled compound.

Melting Point: 230°–231° C.

Rf Value: 0.58 (CHCl$_3$/MeOH=5:1, v/v)

NMR (CDCl$_3$, TMS) δ(ppm): 1.08 (1H, m), 1.37 (3H, s), 1.54 (3H, s), 1.73 (1H, m), 1.95 (3H, s), 2.25 (2H, m), 3.09 (1H, m), 3.22 (1H, m), 3.85 (1H, dd, J=7.3, 7.8 Hz), 4.13 (1H, m), 4.32 (1H, m), 4.64 (1H, d, J=7.3 Hz), 5.75 (1H, br s), 6.06 (1H, d, J=7.8 Hz), 6.89 (1H, d, J=8.3 Hz), 7.48 (1H, dd, J=2.0, 8.3 Hz), 7.56 (1H, d, J=2.0 Hz)

EXAMPLE 19

3,4-trans-3,4-Dihydro-2,2-dimethyl-4-(3-methyl-2-oxo-3,4-diazabicyclo[4.1.0]hept-4-en-5-yloxy)-6-pentafluoroethyl-2H-1-benzopyran-3-ol To 1.5 l of diethyl ether was added 12.63 g (33.67 mmol) of 3-bromo-3,4-dihydro-2,2-dimethyl-6-pentafluoroethyl-2H-1-benzopyran-4-ol synthesized according to the process of JP-B-2-237985, and 30.2 g of potassium hydroxide was added thereto, followed by stirring at room temperature for 54 hours. The insoluble material was removed by filtration, and the solvent was removed by distillation under reduced pressure to yield 9.5 g (96.2%) of 3,4-dihydro-2,2-dimethyl-3,4-epoxy-6-pentafluoroethyl-2H-1-benzopyran.

NMR (CDCl$_3$, TMS) δ(ppm): 1.30 (3H, s), 1.60 (3H, s), 3.54 (1H, d, J=4.4 Hz), 3.94 (1H, d, J=4.4 Hz), 6.90 (1H, d, J=8.3 Hz), 7.46 (1H, dd, J=2.0, 8.3 Hz), 7.57 (1H, d, J=2.0 Hz)

To 100 ml of ethyl alcohol were added 2.50 g (8.50 mmol) of the above obtained compound, 1.20 g (8.56 mmol) of (±)-3-methyl-3,4-diazabicyclo[4.1.0]heptane-2,5-dione, and 0.672 g (8.50 mmol) of pyridine, and the mixture was heated under reflux for 20 hours. The solvent was removed by distillation under reduced pressure. Purification of the residue by silica gel column chromatography gave 1.22 g (33.0%) of the titled compound.

Melting Point: 190°–191° C.

Rf Value: 0.31 (ethyl acetate)

NMR (CDCl$_3$, TMS) δ(ppm): 0.99 (1H, m), 1.35 (3H, s), 1.53 (3H, s), 1.69 (1H, m), 2.17–2.30 (2H, m), 3.25 (3H, s), 3.79 (1H, d, J=3.4 Hz), 3.96 (1H, dd, J=3.4, 7.3 Hz), 5.75 (1H, d, J=7.3 Hz), 6.95 (1H, d, J=8.8 Hz), 7.45 (1H, d, J=8.8 Hz), 7.53 (1H, s)

EXAMPLE 20

3,4-trans-3,4-Dihydro-2,2-dimethyl-3-hydroxy-4-(3-methyl-2-oxo-3,4-diazabicyclo[4.1.0]hept-4-en-5-yloxy)-2H-1-benzopyran-6,7-dicarboxyimide The above-identified compound is a racemate composed of a compound (Iq) shown below wherein the configuration at the 3-, 4-, 1'-, and 6'-positions is S, R, S, and R, respectively, and its optical antipode, or a racemate composed of a compound (Iq) wherein the configuration at the above positions is S, R, R, and S, respectively, and its optical antipode.

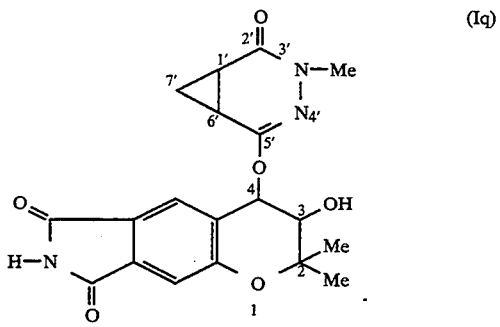

(Iq)

In 20 ml of DMF was dissolved 0.76 g (3.10 mmol) of 3,4-dihydro-2,2-dimethyl-3,4-epoxy-2H-1-benzopyran-6,7-dicarboxyimide obtained in Reference Example 30, and 0.44 g (3.14 mmol)of (±)-3-methyl-3,4-diazabicyclo[4.1.0]heptane-2,5-dione and 0.6 ml (7.43 mmol) of pyridine were added to the solution. The mixture was stirred at 90° C. for 38 hours. The reaction mixture was concentrated under reduced pressure, and ethyl acetate and water were added thereto, followed by stirring. The organic layer was separated, and the aqueous layer was further extracted with ethyl acetate. The organic layers were combined and dried. The solvent was removed under reduced pressure, and the residue was purified by silica gel column chromatography and recrystallized from a mixed solvent of methyl alcohol and isopropyl ether to obtain 62 mg of the titled compound.

Melting Point: 250°–253° C.

Rf Value: 0.40 (CHCl$_3$/MeOH=20:1, v/v)

NMR (DMSO-d$_6$, TMS) δ(ppm): 0.8–1.1 (1H, m), 1.30 (3H, s), 1.43 (3H, s), 1.5–1.9 (1H, m), 2.0–2.4 (2H, m), 3.14 (3H, s), 3.85 (1H, t, J=5.4 Hz), 5.77 (1H, d, J=7.0 Hz), 5.98 (1H, d, J=5.3 Hz), 7.16 (1H, s), 7.65 (1H, s), 11.23 (1H, s)

EXAMPLE 21

(3S, 4R, 1'S, 6'R)-4-(3-Benzyl-2-oxo-3,4-diazabicyclo[4.1.0]hept-4-en-5-yloxy)-3,4-dihydro-2,2-dimethyl-3-hydroxy-2H-1-benzopyran-6-carbonitrile To 20 ml of ethyl alcohol were added 800 mg (3.7 mmol) of (±)-3-benzyl-3,4-diazabicyclo[4.1.0]heptane-2,5-dione obtained in Reference Example 1, 774 mg (3.7 mmol) of (−)-(3S, 4S)-3,4-dihydro-2,2-dimethyl-3,4-epoxy-2H-1-benzopyran-6-carbonitrile, and 0.4 ml of pyridine, and the mixture was heated under reflux for 16 hours. The solvent was removed by distillation under reduced pressure, and the residue was purified by silica gel column chromatography and recrystallized from isopropyl ether to obtain 490 mg (31.7%) of the titled compound.

X-ray structural analysis revealed the S and R configuration at the 1'- and 6'-positions, respectively.

Melting Point: 118°–120° C.

Rf Value: 0.50 (CHCl$_3$/MeOH=20:1, v/v)

$[\alpha]_D^{25}$: −212.8° (c=1, MeOH)

NMR (CDCl$_3$, TMS) δ(ppm): 1.01 (1H, m), 1.25 (3H, s), 1.44 (3H, s), 1.73 (1H, m), 2.18 (1H, m), 2.33 (1H, m), 3.00 (1H, d, J=4.3 Hz), 3.76 (1H, dd, J=4.3, 7.3 Hz), 4.75 (1H, d, J=14.4 Hz), 4.85 (1H, d, J=14.4 Hz), 5.60 (1H, d, J=7.8 Hz), 6.88 (1H, d, J=8.3 Hz), 7.30 (5H, m), 7.48 (1H, dd, J=2.0, 8.3 Hz), 7.52 (1H, s)

EXAMPLES 22 TO 46

Compounds shown in Table 3 below were synthesized in the same manner as in Example 21. The melting point (m.p.), Rf value in silica gel TLC, specific rotation, and NMR data of the compounds are also shown. The NMR spectra were run in CDCl₃, except where noted. The specific rotation was measured at 25° C., except where noted.

TABLE 3

| Example No. | Compound | m.p. (°C.) | Rf (Developing Solvent) | $[\alpha]_D^{25}$ (c = 1, MeOH) (°) | NMR Data (CDCl$_3$, TMS)δ (ppm) |
|---|---|---|---|---|---|
| 22 | (3S,4R,1'R*,6'S*)-3,4-dihydro-2,2-dimethyl-3-hydroxy-4-(3-methyl-2-oxo-3,4-diazabicyclo(4.1.0]hept-4-en-5-yloxy)-2H-benzopyran-6-carbonitrile | | 0.33 (EtOAc) | −150.4 | 1.03(1H, m), 1.33(3H, s), 1.53(3H, s), 1.73(1H, m), 2.20(1H, m), 2.25(1H, m); 3.24(3H, s), 3.93(1H, d, J=7.8Hz), 4.21(1H, br s), 5.73 (1H, d, J=7.8Hz), 6.91(1H, d, J=8.5Hz), 7.51(1H, dd, J=2.0, 8.5Hz), 7.61(1H, d, J=2.0Hz) |
| 23 | (3S,4R,1'R*,6'S*)-4-(3-allyl-2-oxo-3,4-diazabicyclo[4.1.0]-hept-4-en-5-yloxy)-3,4-dihydro-2,2-dimethyl-3-hydroxy-2H-1-benzopyran-6-carbonitrile | 87–89 | 0.42 (CHCl$_3$/MeOH = 10:1, v/v) | −215.5 | 1.04(1H, m), 1.31(3H, s), 1.51(3H, s), 1.73(1H, m), 2.22(1H, m), 2.29(1H, m), 3.83(1H, br s), 3.91(1H, d, J=7.8Hz), 4.16(1H, dd, J=6.3, 15.1Hz), 4.31(1H, dd, J=5.4, 15.1Hz), 5.18–5.26(2H, m), 5.71(1H, d, J=7.8Hz), 5.77–5.88(1H, m) 6.91(1H, d, J=8.3Hz), 7.50 (1H, dd, J=2.0, 8.3Hz), 7.65 (1H, br s) |
| 24 | (3S, 4R, 1'R*,6'S*)-3,4-dihydro-2,2-dimethyl-3-hydroxy-4-(2-oxo-3-(2-propyn-1-yl)-3,4-diazabicyclo[4.1.D]hept-4-en-5-yloxy)-2H-1-benzopyran-6-carbonitrile | 88–90 | 0.47 (CHCl$_3$/MeOH = 10:1, v/v) | −232.2 | 1.10(1H, m), 1.35(3H, s) 1.52(3H, s), 1.75(1H, m), 2.23(2H, m), 2.31(1H, m), 3.54(1H, d, J=3.4Hz), 3.95 (1H, dd, J=7.3, 3.4Hz), 4.34 (1H, dd, J=2.4, 17.1Hz), 4.54 (1H, dd, J=2.0, 17.1Hz), 5.80 (1H, d, J=7.3Hz), 6.92(1H, d, J=8.3Hz), 7.51(1H, dd, J=2.0, 8.3Hz), 7.72(1H, br s) |
| 25 | 3S,4R,1'R*,6'S*)-3,4-dihydro-2,2-dimethyl-3-hydroxy-4-(3-(2-methoxyethyl)-2-oxo-3,4-diazabicyclo(4.1.0]hept-4-en-5-yloxy)-2H-1-benzopyran-6-carbonitrile | | 0.50 (CHCl$_3$/MeOH = 10:1, v/v) | −165.0 | 1.03(1H, m), 1.33(3H, s), 1.51(3H, s), 1.72(1H, m), 2.20(1H, m), 229(1H, m), 3.35(1H, s), 3.57(1H, m), 3.63–3.69(2H, m), 3.88(1H, dd, J=4.9, 7.8Hz), 3.96(1H, m), 3.99(1H, d, J=4.9Hz), 5.82(1H, d, J=7.8Hz), 6.90 (1H, d, J=8.3Hz), 7.50(1H, dd, J=2.0, 8.3Hz), 7.64(1H, d, J=2.0Hz) |
| 26 | (3S,4R,1'R*,6'S*)-3,4-dihydro-2,2-dimethyl-3-hydroxy-4-(3-(2-hydroxyethyl)-2-oxo-3,4-diazabicyclo[4.1.0]hept-4-en-5-yloxy)-2H-1-benzopyran-6-carbonitrile | | 0.14 (EtOAc) | −142.2 | 1.08(1H, m), 1.33(3H, s), 1.51(3H, s), 1.63(1H, s), 1.76(1H, m), 2.23(1H, m), 2.31(1H, m), 3.64(1H, m), 3.87(2H, m), 3.91(1H, d, J=7.3Hz), 4.04(1H, m), 5.78 (1H, d, J=7.3Hz), 6.91 (1H, d, J=8.3Hz), 7.50(1H, dd, J=2.0, 8.3Hz), 7.62(1H, d, J=2.0Hz) |
| 27 | (3S,4R,1'R*,6'S*)-3,4-dihydro-2,2-dimethyl-3-hydroxy-4-(2-oxo-2-phenethyl-3,4-diazabicyclo[4.1.0]hept-4-en-5-yloxy)-2H-1-benzopyran-6-carbonitrile | | 0.47 (CHCl$_3$/MeOH = 10:1, v/v) | −107.4 | 0.77(1H, m), 1.33(3H, s), 1.52(3H, s), 1.59–1.66(1H, m), 2.04–2.17(1H, m), 2.21–2.27(1H, m), 2.86–2.99(2H, m), 3.63–3.71(2H, m), 3.86 (1H, dd, J=3.4, 7.3Hz), 4.12–4.20(1H, m), 5.50(1H, d, J=7.3Hz), 6.91(1H, d, J=8.3Hz), 7.13–7.31(5H, m), 7.51(1H, dd, J=2.0, 8.3Hz), 7.55(1H, br s) |
| 28 | (3S,4R,1'R*,6'S*)-4-(3-(2,2-diethoxyethyl)-2-oxo-3,4-diazabicyclo[4.1.0]hept-4-en-5-yloxy)-3,4-dihydro-2,2-dimethyl-3-hydroxy-2H-1-benzopyran-6-carbonitrile | | 0.18 (CHCl$_3$/MeOH = 40:1, v/v) | −146.0 (20° C.) | 1.02(1H, m), 1.18–1.23(6H), 1.32(3H, s), 1.51(3H, s), 1.73(1H, td, J=9.3, 4.9Hz), 2.17–2.33(2H, m), 3.50–3.62 (2H, m), 3.66–3.82(5H, m), 3.89(1H, dd, J=7.8, 4.4Hz), 4.79(1H, dd, J=6.4, 5.4Hz), 5.75(1H, d, J=7.8Hz), 6.91 (1H, d, J=8.3Hz), 7.50(1H, dd J=8.3, 1.5Hz), 7.62(1H, d, J=1.5Hz) |

TABLE 3-continued

| Example No. | Compound | m.p. (°C.) | Rf (Developing Solvent) | $[\alpha]_D^{25}$ (c = 1, MeOH) (°) | NMR Data (CDCl₃, TMS)δ (ppm) |
|---|---|---|---|---|---|
| 29 | (3S,4R,1'R*,6'S*)-3,4-dihydro-2,2-dimethyl-3-hydroxy-4-(3-(3-methyl-2-buten-1-yl)-2-oxo-3,4-diazabicyclo[4.1.0]hept-4-en-5-yloxy)-2H-1-benzopyran-6-carbonitrile | 82–83 | 0.56 (CHCl₃/MeOH = 10:1, v/v) | −247.6 | 1.02(1H, m), 1.29(3H, s), 1.52(3H, s), 1.71(3H, s), 1.74(3H, s), 1.50–1.80(1H, m), 2.17–2.30(2H, m), 3.90 (1H, d, J=7.8Hz), 4.13(1H, dd, J=7.8, 14.7Hz), 4.34(1H, dd, J=6.9, 14.7Hz), 5.19–5.20(1H, m), 5.70(1H, d, J=7.9Hz), 6.90 (1H, d, J=8.3Hz), 7.50(1H, dd, J=1.9, 8.3Hz), 7.64(1H, s) |
| 30 | (3S,4R,1'R*,6'S*)-3,4-dihydro-2,2-dimethyl-3-hydroxy-4-(3-(2-methyl-2-propen-1-yl)-2-oxo-3,4-diazabicyclo[4.1.0]hept-4-en-5-yloxy)-2H-1-benzopyran-6-carbonitrile | 138–140 | 0.54 (CHCl₃/MeOH = 10:1, v/v) | −238.6 | 1.03(1H, m), 1.30(3H, s), 1.51(3H, s), 1.71(3H, s), 1.67–1.78(1H, m), 2.20–2.35 (2H, m), 3.75–3.80(1H, br s) 3.90(1H, d, J=7.8Hz), 4.13 (1H, d, J=15.1Hz), 4.25(1H, d J=15.1Hz), 4.82(1H, s), 4.96 (1H, s), 5.70(1H, d, J=7.8Hz) 6.91(1H, d, J=8.3Hz), 7.50 (1H, dd, J=2.0, 8.3Hz), 7.64 (1H, d, J=2.0Hz) |
| 31 | (3S,4R,1'R*,6'S*)-3,4-dihydro-2,2-dimethyl-3-hydroxy-4-(3-isobutyl-2-oxo-3,4-diazabicyclo-(4.1.0]hept-4-en-5-yloxy)-2H-1-benzopyran-6-carbonitrile | 177–180 | 0.53 (CHCl₃/MeOH = 10:1, v/v) | −216.2 | 0.89(3H, d, J=6.8Hz), 0.92 (3H, d, J=6.8Hz), 0.97(1H, m) 1.33(3H, s), 1.53(3H, s), 1.72(1H, m), 2.01(1H, m), 2.20(1H, m), 2.30(1H, m), 3.18(1H, dd, J=6.8, 13.7Hz), 3.73(1H, dd, J=7.8, 13.7Hz), 3.87(1H, d, J=3.4Hz), 3.92 (1H, dd, J=3.4, 7.8Hz), 5.69 (1H, d, J=7.8Hz), 6.91(1H, d, J=8.3Hz), 7.50(1H, dd, J=1.9, 8.3Hz), 7.65(1H, br s) |
| 32 | (3S,4R,1'R*,6'S*)-4-(3-n-butyl-2-oxo-3,4-diazabicyclo(4.1.0]-hept-4-en-5-yloxy)-3,4-dihydro-2,2-dimethyl-3-hydroxy-2H-1-benzopyran-6-carbonitrile | | 0.37 (EtOAc) | −173.4 | 0.93(3H, t, J=7.3Hz), 0.93 (1H, m), 1.33(3H, s), 1.33 (1H, m), 1.53(1H, s), 1.59 (2H, m), 1.72(1H, m), 2.20 (1H, m), 2.27(1H, m), 3.47 (1H, m), 3.77(1H, m), 3.87 (1H, d, J=2.9Hz), 3.92(1H, dd, J=2.9, 7.8Hz), 5.70(1H, d, J=7.8Hz), 6.91(1H, d, J= 8.3Hz), 7.51(1H, dd, J=2.0, 8.3Hz), 7.65(1H, d, J=2.0Hz) |
| 33 | (3S,4R,1'R*,6'S*)-4-(3-(2-chlorobenzyl)-2-oxo-3,4-diaza-bicyclo[4.1.0]hept-4-en-5-yloxy)-3,4-dihydro-2,2-dimethyl-3-hydroxy-2H-1-benzopyran-6-carbonitrile | 188–190 | 0.41 (CHCl₃/MeOH = 20:1, v/v) | −266.6 | 1.04–1.07(1H, m), 1.24(3H, s)1.46(3H, s), 1.71–1.77 (1H, m), 2.18–2.24(1H, m), 2.31–2.37(1H, m), 3.29(1H, br s), 3.80(1H, d, J=7.8Hz), 4.72(1H, d, J=14.6Hz), 5.18 (1H, d, J=14.6Hz), 5.60(1H, d, J=7.8Hz), 6.85(1H, d, J= 8.3Hz), 7.20–7.29(3H, m), 7.33–7.36(2H, m), 7.38–7.46 (1H, m) |
| 34 | (3S,4R,1'R*,6'S*)-4-(3-(3-chlorobenzyl)-2-oxo-3,4-diaza-bicyclo[4.1.0]hept-4-en-5-yloxy)-3,4-dihydro-2,2-dimethyl-3-hydroxy-2H-1-benzopyran-6-carbonitrile | 165–167 | 0.58 (CHCl₃/MeOH = 10:1-1 v/v) | −182.6 | 1.04(1H, m), 1.30(3H, s), 1.46(3H, s), 1.72–1.78(1H, m), 2.16–2.22(1H, m), 2.30–2.36(1H, m), 3.05(1H, d, J= 4.4Hz), 3.79–3.82(1H, m), 4.65(1H, d, J=14.2Hz), 4.86 (1H, d, J=14.2Hz), 5.64(1H, d, J=7.3Hz), 6.89(1H, d, J= 8.8Hz), 7.22–7.32(4H, m), 7.49(1H, dd, J=2.0, 8.8Hz), 7.53(1H, s) |
| 35 | (3S,4R,1'R*,6'S*)-4-(3-(4-chlorobenzyl)-2-oxo-3,4-diaza-bicyclo(4.1.0]hept-4-en-5-yloxy)-3,4-dihydro-2,2-dimethyl-3-hydroxy-2H-1-benzopyran-6-carbonitrile | 163–164 | 0.40 (CHCl₃/MeOH = 20:1, v/v) | −182.0 (27° C.) | 0.98–1.01(1H, m), 1.28(3H, s), 1.47(3H, s), 1.70–1.75 (1H, m), 2.16–2.21(1H, m), 2.27–2.33(1H, m), 3.31(1H, br s), 3.81(1H, d, J=7.3Hz), 4.71(1H, d, J=14.6Hz), 4.76 1H, d, J=14.6Hz), 5.63(1H, d, J=7.3Hz), 6.89(1H, d, J= 8.3Hz), 7.24–7.30(4H, m), 7.49(1H, dd, J=8.3, 1.9Hz), 7.53(1H, s) |
| 36 | (3S,4R,1'R*,6'S*)-4-(3-(2,6- | 255–256 | 0.38 | −411.2 | (DMSO-d₆, TMS)0.77–0.81(1H, |

TABLE 3-continued

| Example No. | Compound | m.p. (°C.) | Rf (Developing Solvent) | $[\alpha]_D^{25}$ (c = 1, MeOH) (°) | NMR Data (CDCl$_3$, TMS)δ (ppm) |
|---|---|---|---|---|---|
| | dichlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile | | (CHCl$_3$/MeOH = 20:1, v/v) | (26° C.) | m), 1.14(3H, s), 1.41(3H, s) 1.72–1.78(1H, m), 2.27–2.33 (2H, m), 3.64(1H, dd, J=5.4, 8.8Hz), 4.68(1H, d, J=13.7Hz) 5.27(1H, d, J=13.7Hz), 5.54 (1H, d, J=8.8Hz), 6.00(1H, d, J=5.4Hz), 6.70(1H, s), 6.88 (1H, d, J=8.3Hz), 7.17–7.21 (1H, m), 7.28–7.30(2H, m), 7.55(1H, dd, J=2.0, 8.3Hz) |
| 37 | (3S,4R,1'R*,6'S*)-4-(3-(2,4-dichlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile | | 0.44 (CHCl$_3$/MeOH = 20:1, v/v) | −221.6 (24° C.) | 1.03–1.06(1H, m), 1.25(3H, s), 1.47(3H, s), 1.72–1.78 (1H, m), 2.19–2.24(1H, m), 2.32–2.37(1H, m), 3.20(1H, d, J=3.9Hz), 3.82(1H, dd, J= 3.9, 7.8Hz), 4.72(1H, d, J= 14.6Hz), 5.09(1H, d, J=14.6 Hz), 5.58(1H, d, J=7.8Hz), 6.87(1H, d, J=8.3Hz), 7.20–7.26(2H, m), 7.37(1H, d, J= 2.0Hz), 7.43–7.48(2H, m) |
| 38 | (3S,4R,1'R*,6'S*)-3,4-dihydro-2,2-dimethyl-3-hydroxy-4-(3-(2-methylbenzyl)-2-oxo-3,4-diazabicyclo[4.1.0]hept-4-en-5-yloxy)-2H-1-benzopyran-6-carbonitrile | | 0.18 (CHCl$_3$/MeOH = 40:1, v/v) | −249.5 (26° C.) | (DMSO-d$_6$, TMS)0.96(1H, m), 1.19(3H, s), 1.40(3H, s), 1.71(1H, td, J=9.3, 4.4Hz), 2.20–2.30(2H, m), 2.26(3H, s), 3.75(1H, dd, J=7.3, 5.4Hz), 4.52(1H, d, J=15.1Hz), 4.93(1H, d, J=15.1Hz), 5.57 (1H, d, J=7.3Hz), 5.92(1H, d, J=5.4Hz), 6.94(1H, d, J=8.3Hz), 7.12(4H, s), 7.43(1H, s), 7.63(1H, d, J=8.3Hz) |
| 39 | (3S,4R,1'R*,6'S*)-3,4-dihydro-2,2-dimethyl-3-hydroxy-4-(3-(4-methylbenzyl)-2-oxo-3,4-diazabicyclo[4.1.0]hept-4-en-5-yloxy)-2H-1-benzopyran-6-carbonitrile | | 0.26 (CHCl$_3$/MeOH = 40:1, v/v) | −226.1 | (DMSO-d$_6$, TMS)0.91(1H, m), 1.23(3H, s), 1.40(3H, s), 1.67(1H, td, J=9.3, 4.4Hz), 2.20–2.30(2H, m), 2.26(3H, s), 3.77(1H, dd, J=7.3, 5.4Hz), 4.52(1H, d, J=14.2Hz), 4.79(1H, d, J=14.2Hz), 5.63 (1H, d, J=7.3Hz), 5.90(1H, d, J=5.4Hz), 6.96(1H, d, J= 8.8Hz), 7.10(2H, d, J=8.3Hz), 7.14(2H, d, J=8.3Hz), 7.54(1H, d, J=2.0Hz), 7.65(1H, dd, J=8.8, 2.0Hz) |
| 40 | (3S,4R,1'R*,6'S*)-3,4-dihydro-2,2-dimethyl-3-hydroxy-4-(3-(4-methoxybenzyl)-2-oxo-3,4-diazabicyclo[4.1.0]hept-4-en-5-yloxy)-2H-1-benzopyran-6-carbonitrile | | 0.17 (CHCl$_3$/MeOH = 40:1, v/v) | −205.1 (24° C.) | (DMSO-d$_6$, TMS)0.91(1H, m), 1.24(3H, s), 1.40(3H, s), 1.66(1H, td, J=9.3, 4.4Hz), 2.22(2H, dd, J=8.8, 4.9Hz), 3.71(3H, s), 3.78(1H, dd, J= 6.8, 5.4Hz), 4.54(1H, d, J= 14.7Hz), 4.73(1H, d, J=14.7Hz) 5.63(1H, d, J=6.8Hz), 5.90(1H d, J=5.4Hz), 6.85(2H, d, J=8.8 Hz), 6.96(1H, d, J=8.8Hz), 7.20(2H, d, J=8.8Hz), 7.59 (1H, d, J=2.0Hz), 7.66(1H, dd, J=8.8, 2.0Hz) |
| 41 | (3S,4R,1'R*,6'S*)-3,4-dihydro-2,2-dimethyl-3-hydroxy-4-(3-(4-hydroxybenzyl)-2-oxo-3,4-diazabicyclo[4.1.0]hept-4-en-5-yloxy)-2H-1-benzopyran-6-carbonitrile | 213–215 | 0.27 (CHCl$_3$/MeOH = 20:1, v/v) | | 0.90(1H, m), 1.32(3H, s), 1.48(3H, s), 1.62–1.67(1H, m), 1.97(6H, br s), 2.11–2.17 (1H, m), 2.21–2.26(1H, m), 3.83–3.85(1H, m), 4.57(1H, d, J=14.1Hz), 4.78(1H, d, J= 14.1Hz), 5.73(1H, d, J=7.3Hz) 6.77(2H, d, J=8.8Hz), 6.88 (2H, d, J=8.3Hz), 7.14(2H, d, J=8.3Hz), 7.45–7.48(2H, m) |
| 42 | (3S,4R,1'R*,6'S*)-4-(3-(3,5-di-t-butyl-4-hydroxybenzyl)-2-oxo-3,4-diazabicyclo-[4.1.0]hept-4-en-5-yloxy)-3,4-dihydro-2,2-dimethyl-3-hydroxy-2H-1-benzopyran-6-carbonitrile | | 0.70 (EtOAc) | −124.7 | 1.01(1H, m), 1.25(3H, s), 1.42(18H, s), 1.47(3H, s), 1.72(1H, m), 2.17,(1H, m), 2.31(1H, m), 3.79(1H, d, J= 7.8Hz), 4.54(1H, d, J=14.1Hz) 4.84(1H, d, J=14.1Hz), 5.18 (1H, s), 5.60(1H, d, J=7.8Hz) 6.89(1H, d, J=8.3Hz), 7.13 (2H, s), 7.49(1H, dd, J=2.0, 8.3Hz), 7.58(1H, d, J=2.0Hz) |

TABLE 3-continued

| Example No. | Compound | m.p. (°C.) | Rf (Developing Solvent) | $[\alpha]_D^{25}$ (c = 1, MeOH) (°) | NMR Data (CDCl$_3$, TMS)δ (ppm) |
|---|---|---|---|---|---|
| 43 | (3s,4R,1'R*,6'S*)-3,4-dihydro-2,2-dimethyl-4-(3-(3,5-dimethyl-4-hydroxybenzyl)-2-oxo-3,4-diazabicyclo[4.1.0]hept-4-en-5-yloxy)-3-hydroxy-2H-1-benzopyran-6-carbonitrile | | 0.60 (EtOAc) | −171.1 | 0.98(1H, m), 1.32(3H, s), 1.49(3H, s), 1.69(1H, m), 2.15(1H, m), 2.18(6H, s), 2.27(1H, m), 3.70(1H, d, J=4.4Hz), 3.81(1H, dd, J=4.4, 7.8Hz), 4.57(1H, d, J=14.1Hz), 4.64(1H, d, J=14.1Hz), 5.09 (1H, s), 5.72(1H, d, J=7.8Hz), 6.89(1H, d, J=8.3Hz), 6.93 (2H, s), 7.40–7.50(2H, m) |
| 44 | (3S,4R,1'R*,6'S*)-3,4-dihydro-2,2-dimethyl-3-hydroxy-4-(2-oxo-3-(4-sulfamoylbenzyl)-3,4-diazabicyclo(4.1.0]hept-4-en-5-yloxy)-2H-1-benzopyran-6-carbonitrile | | 0.37 (CHCl$_3$/MeOH = 10:1, v/v) | −149.3 | 0.93(1H, m), 1.32(3H, s), 1.50(3H, s), 1.71(1H, m), 2.21(1H, m), 2.31(1H, m), 3.38(1H, br s), 3.88(1H, d, J=7.3Hz), 4.51(1H, d, J=14.7 Hz), 5.17(1H, d, J=14.7Hz), 5.39(2H, s), 5.73(1H, d, J=7.3Hz), 6.88(1H, d, J=8.3Hz), 7.40(2H, d, J=8.3Hz), 7.41 (1H, d, J=2.0Hz), 7.45(1H, dd, J=8.3, 2.0Hz), 7.86(2H, d, J=8.3Hz) |
| 45 | (3S,4R,1'R*,6'S*)-3,4-dihydro-2,2-dimethyl-4-(3-(2-fluorobenzyl)-2-oxo-3,4-diazabicyclo-4.1.0]hept-4-en-5-yloxy)-3-hydroxy-2H-1-benzopyran-6-carbonitrile | | 0.38 (CHCl$_3$/MeOH = 20:1, v/v) | −236.4 (28° C.) | 0.98–1.02(1H, m), 1.29(3H, s) 1.47(3H, s), 1.68–1.74(1H, m) 2.17–2.22(1H, m), 2.28–2.33 (1H, m), 3.44(1H, br s), 3.82 (1H, d, J=7.8Hz), 4.72(1H, d, J=14.6Hz), 5.02(1H, d, J=14.6 Hz), 5.66(1H, d, J=7.8Hz), 6.87(1H, d, J=8.3Hz), 7.00–7.04(1H, m), 7.09–7.13(1H, m) 7.24–7.33(2H, m), 7.44(1H, s) 7.47(1H, d, J=2.0Hz) |
| 46 | (3S,4R,1'R*,6'S*)-3,4-dihydro-2,2-dimethyl-4-(3-(4-fluorobenzyl)-2-oxo-3,4-diazabicyclo[4.1.0]hept-4-en-5-yloxy)-3-hydroxy-2H-1-benzopyran-6-carbonitrile | | 0.41 (CHCl$_3$/MeOH = 20:1, v/v) | | 0.96–1.00(1H, m), 1.29(3H, s) 1.48(3H, s), 1.68–1.74(1H, m) 2.16–2.21(1H, m), 2.26–2.31 (1H, m), 3.82(1H, d, J=7.8Hz), 4.73(2H, s), 5.66(1H, d, J=7.8Hz), 6.89(1H, d, J=8.8Hz), 6.98–7.03(2H, m), 7.27–7.31 (2H, m), 7.48(1H, dd, J=2.0, 8.8Hz), 7.53(1H, d, J=2.0Hz) |

EXAMPLE 47

(3S,4R,1'R*,6'S*)-3,4-Dihydro-2,2-dimethyl-3-hydroxy-4-(2-oxo-3,4-diazabicyclo[4.1.0]-hept-4-en-5-yloxy)-2H-1-benzopyran-6-carbonitrile

Process A

To 500 ml of ethanol were added 12.33 g (97.7 mmol) of (+)-3,4-diazabicyclo[4.1.0]heptane-2,5-dione prepared in Reference Example 28, 18.6 g (92.5 mmol) of (3S,4S) -3,4-dihydro-2,2-dimethyl-3,4-epoxy-2H-1-benzopyran-6-carbonitrile, and 7.5 ml (92.5 mmol) of pyridine, followed by heating under reflux for 14 hours. The solvent was removed by distillation under reduced pressure, and the residue was purified by silica gel column chromatography and high performance liquid chromatography to obtain 2.4 g (7.9 %) of the titled compound.

Rf Value: 0.29 (ethyl acetate)

$[\alpha]_D^{25}$: −168.1° (c=1, MeOH)

NMR (CDCl$_3$, TMS) δ(ppm): 1.18 (1H, m), 1.33 (3H, s), 1.52 (3H, s), 1.60–2.10 (1H, br s), 1.81 (1H, m), 2.21 (2H, m), 3.92 (1H, d, J=7.3 Hz), 5.71 (1H, d, J=7.3 Hz), 6.91 (1H, d, J=8.3 Hz), 7.50 (1H, dd, J=2.0, 8.3 Hz), 7.59 (1H, d, J=2.0 Hz), 7.71 (1H, s)

Process B

To 450 ml of 1,2-dichloroethane were added 5.91 g (13.2 mmol) of (3S, 4R, 1'R*, 6'S*)-3,4-dihydro-2,2-dimethyl-3-hydroxy-4-(3-(4-methoxybenzyl)-2-oxo-3,4-diazabicyclo-[4.1.0]hept-4-en-5-yloxy)-2H-1-benzopyran-6-carbonitrile obtained in Example 40, and 17.7 g (78 mmol) of 2,3-dichloro-5,6-dicyano-1,4-benzoquinone and 0.9 ml (50 mmol) of water were added thereto, followed by heating under reflux for 8 hours. The insoluble matter was removed by filtration, and the filtrate was concentrated under reduced pressure. Purification by silica gel column chromatography furnished 2.81 g (65.1%) of the titled compound.

EXAMPLE 48

(3S,4R,1'R*,6'S*)-4-(3-Cyanomethyl-2-oxo-3,4-diazabicyclo[4.1.0]hept-4-en-5-yloxy)-3,4-dihydro-2,2-dimethyl-3-hydroxy-2H-1-benzopyran-6-carbonitrile To 3 ml of acetone were added 200 mg (0.61 mmol) of (3S,4R,1'R*,6'S*)-3,4-dihydro-2,2-dimethyl-3-hydroxy-4-(2-oxo-3,4-diazabicyclo[4.1.0]hept-4-en-5-yloxy)-2H-1-benzopyran-6-carbonitrile obtained in Example 47 and 85 mg (0.61 mmol) of potassium carbonate, followed by stirring. To the mixture was added a solution of 147 mg (1.22 mmol) of bromoacetonitrile in 2 ml of acetonitrile, followed by heating under reflux for 4 hours. To the mixture were further added 585 mg (4.88 mmol) of bromoacetonitrile and 170 mg (1.22 mmol) of potassium carbonate, followed by heating under reflux for 3 hours. The insoluble material was removed by filtration, and the solvent was removed by distillation under reduced pressure. Water was added to the residue, and the mixture was extracted with ethyl acetate. The organic layer was washed with water and then with a saturated sodium chloride aqueous solution, and dried over anhydrous sodium sulfate. The solvent was removed by distillation under reduced pressure, and the residue was purified by silica gel column chromatography to give 81 mg (36.3%) of the titled compound.

Rf Value: 0.47 (ethyl acetate)

$[\alpha]_D^{25}$: −168.4° (c=1, MeOH)

NMR (CDCl$_3$, TMS) δ(ppm): 1.18 (1H, m), 1.39 (3H, s), 1.50 (3H, s), 1.82 (1H, m), 2.26 (1H, m), 2.34 (1H, m), 2.82 (1H, d, J=5.4 Hz), 3.97 (1H, dd, J=5.4, 6.9 Hz), 4.36 (1H, d, J=17.1 Hz), 4.79 (1H, d, J=17.1 Hz), 5.82 (1H, d, J=6.9 Hz), 6.93 (1H, d, J=8.8 Hz), 7.52 (1H, dd, J=2.0, 8.8 Hz), 7.60 (1H, d, J=2.0 Hz)

EXAMPLES 49 TO 52

Compounds shown in Table 4 below were synthesized in the same manner as in Example 48. The melting point (m.p.), Rf value in silica gel TLC, specific rotation, and NMR data of the compounds are also shown. The NMR spectra were run in CDCl$_3$, except where noted. The specific rotation was measured at 25° C., except where noted.

EXAMPLE 53

(3S,4R,1′R*,6′S*)-3,4-Dihydro-2,2-dimethyl-3-hydroxy-4-(3-methyl-2-oxo-3,4-diazabicyclo[4.1.0]-hept-4-en-5-ylamino]-2H-1-benzopyran-6-carbonitrile In 25 ml of dimethyl sulfoxide was dissolved 557 mg (4.0 mmol) of (±)-2-amino-4-methyl-3,4-diazabicyclo[4.1.0]hept-2-en-5-one obtained in Reference Example 29, and 160 mg (4 mmol) of 60% sodium hydride and 885 mg (4.4 mmol) of (3S,4S)-3,4-dihydro-2,2-dimethyl-3,4-epoxy-2H-1-benzopyran-6-carbonitrile were added to the solution, followed by stirring at room temperature for 4 hours. Water was added to the reaction mixture, followed by extraction with ethyl acetate. The organic layer was washed with water and then with a saturated sodium chloride aqueous solution and dried over anhydrous sodium sulfate. The solvent was removed by distillation under reduced pressure, and the residue was purified by silica gel column chromatography and recrystallized from ethyl acetate to obtain 152 mg (11.1%) of the titled compound.

Melting Point: 157°–158° C.

Rf Value: 0.24 (CHCl$_3$/MeOH=10:1, v/v)

$[\alpha]_D^{25}$: −217.0° (C=1, MeOH)

NMR (CDCl$_3$, TMS) δ(ppm): 1.00 (1H, m), 1.28 (3H, s), 1.52 (3H, s), 1.66 (1H, m), 2.00 (1H, m), 2.21 (1H, m), 3.22 (3H, s), 3.73 (1H, dd, J=2.0, 8.3 Hz), 4.39 (1H, d, J=7.8 Hz), 4.82 (1H, d, J=2.0 Hz), 4.91 (1H, dd, J=7.8,

TABLE 4

| Example No. | Compound | m.p. (°C.) | Rf (Developing Solvent) | $[\alpha]_D^{25}$ (c = 1, MeOH) (°) | NMR Data (CDCl$_3$, TMS)δ (ppm) |
|---|---|---|---|---|---|
| 49 | (3S,4R,1′R*,6′S*)-3,4-dihydro-2,2-dimethyl-4-(3-ethoxy-carbonylmethyl-2-oxo-3,4-diazabicyclo(4.1.0]hept-4-en-5-yloxy)-3-hydroxy-2H-1-benzo-pyran-6-carbonitrile | | 0.46 (EtOAc) | −157.6 | 1.19(1H, m), 1.29(3H, t, J=6.8Hz), 1.31(3H, s), 1.52(3H, s), 1.77(1H, m), 2.25(1H, m), 2.32(1H, m), 3.92(1H, d, J=7.3Hz), 4.23(2H, q, J=6.8Hz), 4.28(1H, d, J=17.1Hz), 4.46(1H d, J=17.1Hz), 5.75(1H, d, J=7.3 Hz), 6.90(1H, d, J=8.8Hz), 7.50 (1H, dd, J=2.0, 8.0Hz), 7.62 (1H, d, J=2.0Hz) |
| 50 | (3S,4R,1′R*,6′S*)-4-(3-carbamoylmethyl-2-oxo-3,4-diazabicyclo[4.1.0]hept-4-en-5-yloxy)-3,4-dihydro-2,2-dimethyl-3-hydroxy-2H-1-benzopyran-6-carbonitrile | | 0.24 (CHCl$_3$/MeOH = 10:1, v/v) | −157.4 | 1.16(1H, m), 1.33(3H, s), 1.50 (3H, s), 1.79(1H, m), 2.23–2.35 (2H, m), 3.80–3.90(1H), 3.91 (1H, d, J=7.3Hz), 4.00(1H, d, J=15.6Hz), 4.56(1H, d, J=15.6Hz), 5.83(1H, d, J=7.3Hz), 6.90(1H, d, J=8.3Hz), 7.50(1H, dd, J=2.0, 8.3Hz), 7.61(1H, d, J=2.0 Hz) |
| 51 | (3S,4R,1′R*,6′S*)-4-(3-(4-cyanobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile | 185–187 | 0.32 (CHCl$_3$/MeOH = 20:1, v/v) | −198.9 | (DMSO-d$_6$)1.07(1H, m), 1.22 (3H, s), 1.39(3H, s), 1.71(1H, m), 2.27(2H, m), 3.77(1H, dd, J=6.8, 5.4Hz), 4.69(1H, d, J=15.6Hz), 4.93(1H, d, J=15.6Hz), 5.58(1H, d, J=6.8Hz), 5.89(1H, d, J=5.4Hz), 6.95(1H, d, J=8.8 Hz), 7.44(2H, d, J=8.3Hz), 7.54 (1H, s), 7.64(1H, dd, J=8.8, 2.0Hz), 7.77(2H, d, J=8.3Hz) |
| 52 | (3S,4R,1′R*,6′S*)-3,4-dihydro-2,2-dimethyl-3-hydroxy-4-(2-oxo-3-(4-pyridylmethyl)-3,4-diaza-bicyclo[4.1.0]hept-4-en-5-yl-oxy)-2H-1-benzopyran-6-carbonitrile | | 0.64 (CHCl$_3$/MeOH = 5:1, v/v) | −173.4 | 1.07(1H, m), 1.27(3H, s), 1.47 (3H, s), 1.78(1H, m), 2.21(1H, m), 2.32(1H, m), 3.52(1H, br s), 3.84(1H, d, J=7.3Hz), 4.74 (1H, d, J=15.1Hz), 4.84(1H, d, J=15.1Hz), 5.64(1H, d, J=7.3 Hz), 6.89(1H, d, J=8.3Hz), 7.21(1H, br s), 7.48(1H, dd, J=2.0, 8.3Hz), 7.55(1H, d, J=2.0Hz), 8.56(2H, br s) |

8.3 Hz), 6.90 (1H, d, J=8.3 Hz), 7.49 (1H, dd, J=2.0, 8.3 Hz), 7.67 (1H, br s)

EXAMPLE 54

(3S, 4R, 1'S, 6'R)-3-Acetoxy-4-(3-benzyl-2-oxo-3,4-diazabicyclo[4.1.0]hept-4-en-5-yloxy)-3,4-dihydro-2,2-dimethyl-2H-1-benzopyran-6-carbonitrile To 10 ml of methylene chloride was added 0.31 g (0.74 mmol) of (3S,4R,1'S,6'R)-4-(3-benzyl-2-oxo-3,4-diazabicyclo[4.1.0]hept-4-en-5-yloxy)-3,4-dihydro-2,2-dimethyl-3-hydroxy-2H-1-benzopyran-6-carbonitrile obtained in Example 21, and 0.16 ml (2 mmol) of pyridine and 0.16 ml (2 mmol) of acetyl chloride were added thereto dropwise, followed by stirring at room temperature for 1 day. The solvent was removed by distillation under reduced pressure, and the residue was purified by silica gel column chromatography and recrystallized from diisopropyl ether to obtain 0.145 g (42.6%) of the titled compound.

Melting Point: 149°–151° C.
Rf Value: 0.74 (EtOAc)
$[\alpha]_D^{25}$: −92.9° (c=1, MeOH)
NMR (CDCl$_3$, TMS) δ(ppm): 0.94 (1H, m), 1.35 (3H, s), 1.42 (3H, s), 1.64 (1H, m), 1.99 (3H, s), 2.06 (1H, m), 2.29 (1H, m), 4.62 (1H, d, J=14.1 Hz), 4.97 (1H, d, J=14.1 Hz), 5.34 (1H, d, J=5.9 Hz), 5.74 (1H, d, J=5.9 Hz), 6.92 (1H, d, J=8.3 Hz), 7.25–7.35 (5H, m), 7.50 (1H, dd, J=2.0, 8.3 Hz), 7.52 (1H, d, J=2.0 Hz)

EXAMPLE 55

(3S, 4R, 1'R*, 6'S*)-3-Acetoxy-4-(3-(2-chlorobenzyl)-2-oxo-3,4-diazabicyclo[4.1.0]hept-4-en-5-yloxy)-3,4-dihydro-2,2-dimethyl-2H-1-benzopyran-6-carbonitrile The titled compound was obtained in the same manner as in Example 54, except for using (3S,4R,1'R*,6'S*)-4-(3-(2-chlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile obtained in Example 33, instead of the compound obtained in Examples 21.

Rf Value: 0.64 (CHCl$_3$/MeOH=20:1, v/v)
$[\alpha]_D^{27}$: −132.0° (c=1, CHCl$_3$)
NMR (CDCl$_3$, TMS) δ(ppm): 0.99–1.03 (1H, m), 1.32 (3H, s), 1.41 (3H, s), 1.64–1.70 (1H, m), 2.05 (3H, s), 2.07–2.12 (1H, m), 2.29–2.35 (1H, m), 4.67 (1H, d, J=14.6 Hz), 5.22 (1H, d! J=14.6 Hz), 5.30 (1H, d, J=5.4 Hz), 5.71 (1H, d, J=5.4 Hz), 6.89 (1H, d, J=8.8 Hz), 7.19–7.35 (5H, m), 7.46 (1H, dd, J=2.0, 8.8 Hz)

EXAMPLE 56

(3S,4R,1'R*,6'S*)-3,4-Dihydro-3-hydroxy-4-(3-methyl-2-oxo-3,4-diazabicyclo[4.1.0]hept-4-en-5-yloxy)-2,2,3-trimethyl-2H-1-benzopyran-6-carbonitrile In 15 ml of methyl alcohol was dissolved 300 mg (0.85 mmol) of 3,4-trans-3,4-dihydro-3-hydroxy-4-(3-methyl-2-oxo-3,4-diazabicyclo[4.1.0]hept-4-en-5-yloxy)-2,2,3-trimethyl-2H-1-benzopyran-6-carbonitrile obtained in Example 14 and separated into its enantiomers by high performance liquid chromatography ("CHIRALPAK AD"; Daicel Chemical Industries, LTD., ethyl alcohol/hexane=15:85, v/v) . Recrystallization from ethyl acetate/hexane gave 102 mg (34.0%) of the titled compound.

Melting Point: 192°–193° C.
Rf Value: 0.21 (EtOAc)
$[\alpha]_D^{25}$: −162.2° (c=1, EtOAC)
NMR (CDCl$_3$, TMS) δ(ppm): 1.04 (1H, m), 1.25 (3H, s), 1.42 (3H, s), 1.50 (3H, s), 1.74 (1H, m), 2.22–2.35 (2H, m), 3.25 (3H, s), 3.90 (1H, s), 5.83 (1H, s), 6.91 (1H, d, J=8.30 Hz), 7.51 (1H, dd, J=1.95, 8.30 Hz), 7.66 (1H, s)

EXAMPLE 57

(3S,4R,1'R*,6'S*)-4-(3-(2-Chlorobenzyl)-2-oxo-3,4-diazabicyclo[4.1.0]hept-4-en-5-yloxy)-3,4-dihydro-2,2-dimethyl-3-formyloxy-2H-1-benzopyran-6-carbonitrile To 15 ml of benzene were added 1.5 g (3.3 mmol) of (3S,4R,1'R*,6'S*)-4-(3-(2-chlorobenzyl)-2-oxo-3,4-diazabicyclo[4.1.0]hept-4-en-5-yloxy)-3,4-dihydro-2,2-dimethyl-3-hydroxy-2H-1-benzopyran-6-carbonitrile obtained in Example 33 and 5 ml (132.6 mmol) of formic acid, followed by heating under reflux for 19 hours. The reaction mixture was poured into water and extracted with ethyl acetate. The extract was washed successively with a saturated sodium hydrogencarbonate aqueous solution, water, and a saturated sodium chloride aqueous solution, and dried over sodium sulfate. The solvent was removed by distillation under reduced pressure, and the residue was purified by silica gel column chromatography to obtain 0.706 g (44.3%) of the titled compound.

Rf Value: 0.64 (CHCl$_3$/MeOH=20:1, v/v)
$[\alpha]_D^{17}$: −100.6° (c=1, MeOH)
NMR (CDCl$_3$, TMS) δ(ppm): 1.00–1.04 (1H, m), 1.33 (3H, s), 1.43 (3H, s), 1.65–1.71 (1H, m), 2.08–2.13 (1H, m), 2.29–2.35 (1H, m), 4.70 (1H, d, J=15.1 Hz), 5.18 (1H, d, J=15.1 Hz), 5.40 (1H, d, J=6.3 Hz), 5.78 (1H, d, J=6.3 Hz), 6.89 (1H, d, J=8.3 Hz), 7.20–7.34 (5H, m), 7.47 (1H, d, J=8.3 Hz), 8.00 (1H, s)

TEST EXAMPLE 1

Potassium Channel Opening Activity

1) Potassium channel opening activity of test compounds shown in Table 5 below was determined according to the test method of *Naunyn-Schmiedeberg's Archives of Pharmacology*, Vol. 338, pp. 319–326 (1988). $^{86}$Rb was incorporated into a segment of an excised aorta of a Wistar rat, and the segment was surface-perfused with a solution containing a test compound for 10 minutes. The potassium channel opening activity of the test compound was expressed in terms of an effective concentration at which the area under the peak of the $^{86}$Rb release rate reached 0.2 (EC$_{AUC0.2}$). The results obtained are shown in Table 5.

TABLE 5

| Example No. of Test Compound | EC$_{AUC0.2}$ |
|---|---|
| 22 | 0.18 |
| 23 | 0.18 |
| 47 | 0.21 |
| 56 | 0.021 |
| EMD57283 | 0.16 |
| Cromakalim | 2.8 |

Note:
EMD57283: (3S,4R)-3,4-Dihydro-4-((1,6-dihydro-1-methyl-6-oxo-3-pyridazinyl)oxy)-2,2-dimethyl-3-hydroxy-2H-1-benzopyran-6-carbonitrile
Cromakalim: 3,4-trans-3,4-Dihydro-2,2-dimethyl-3-hydroxy-4-(2-oxopyrrolidin-1-yl)-2H-1-benzopyran-6-carbonitrile 2) Twenty-two-week-old male spontaneously hypertensive rats (body weight, 350–420 g) were given an intravenous injection of 30 mg/kg of glibenclamide (Sigma Chemical Company) having an antagonistic activity against potassium channel openers or, as a control, a solvent. Ten minutes later, 0.1 mg/kg of the compound of Example 1 was intravenously administered, and the blood pressure changes were observed for 6 hours after the administration (see, *Journal of Pharmacology and Experimental Therapeutics*, Vol. 248, p.1261 (1989)). The results obtained are shown in Table 6 below.

TABLE 6

| | Average Blood Pressure Fall (mmHg) | | | |
|---|---|---|---|---|
| | 1 Hr. | 2 Hrs. | 3 Hrs. | 4 Hrs. |
| Compound of Ex. 1 (0.1 mg/kg) + solvent (i.v.) | 41.4 ± 6.1 | 50.4 ± 4.4 | 55.9 ± 4.3 | 55.1 ± 4.7 |
| Compound of Ex. 1 (0.1 mg/kg) + Glibenclamide (30 mg/kg) (i.v.) | 15.9 ± 3.7 | 22.0 ± 5.7 | 28.0 ± 5.3 | 26.9 ± 5.7 |

From these results, it was proved that each of the compounds of Examples 1, 22, 23, 47, and 56 possesses potassium channel opening activity.

TEST EXAMPLE 2

Antihypertensive Activity in Spontaneously Hypertensive Rats

Male spontaneously hypertensive rats (16 to 20-week-old; body weight: 300–400 g) fed ab lib. were forceably given oral administration of a test compound suspended in 0.5% (w/v) carboxymethyl cellulose aqueous solution. After 1, 2, 4, 6, 8, 24, 30 or 48 hours from the administration, the systolic blood pressure was measured by a tail-cuff method described in *Arzneimittel-Forschung*, Vol. 18, pp. 1285–1287 (1968)).

The antihypertensive activity of the test compound was obtained as an effective dose for reducing blood pressure by 50 mmHg ($ED_{50mmHg}$). Further, the time of onset of the maximum activity and the maximum increase in heart rate at a dose for reducing blood pressure by 50 to 60 mmHg were measured. The results obtained are shown in Table 7 below.

TABLE 7

| Compound of Example | $ED_{50mmHg}$ (mg/kg) | Time for Onset of Max. Activity (hr) | Max. increase of Heat Rate (%) |
|---|---|---|---|
| 21 | 0.053 | 6.4 ± 0.5** | 19.7 ± 3.0** |
| 24 | 0.020 | 5.6 ± 1.2 | 22.2 ± 2.3** |
| 32 | 0.076 | 6.0 ± 0.6* | 22.3 ± 5.9* |
| 33 | 0.031 | 6.6 ± 0.5** | 19.4 ± 3.1** |
| 36 | 0.40 | 6.8 ± 0.5** | 9.6 ± 1.3** |
| 37 | 0.035 | 7.6 ± 0.4** | 9.2 ± 1.7** |
| 56 | 0.0023 | 6.4 ± 0.4** | 19.2 ± 0.5** |
| EMD57283 | 0.0064 | 2.8 ± 0.7 | 41.3 ± 2.8 |

*$p < 0.05$,
**$p < 0.01$ vs. EMD57283

The statistical difference between a test compound and EMD57283 was analyzed by the Student's t-test.

Each of the compounds of Examples 21, 24, 32, 33, 36, 37, and 56 exhibits a potent antihypertensive activity with, as compared with the reference drug, a slower onset of action and a reduced side effect in increasing the heart rate. Further, these compounds had a long duration of activity.

TEST EXAMPLE 3

Effect on Renal Blood Flow

Twenty-week-old male spontaneously hypertensive rats (body weight: 350–430 g) were anesthetized with pentobarbital (30 mg/kg, i.p.). An incision was made in the abdomen on the left side, and a Doppler probe for blood flow measurement was fitted to the left renal artery, and the code (wire lead) of the probe was passed under the back skin and taken out from the back of the neck. After 1 week from the operation, the code of the probe was connected to a Doppler blood flow meter to start measurement of the renal blood flow. After the renal blood flow reached to a steady state, a test compound was orally administered, and changes in renal blood flow were observed up to 9 hours. The test compound was used at a dose which reduced blood pressure by about 50 mmHg. The results obtained are shown in Table 8 below.

TABLE 8

| Compound of Example | Increase in Renal Blood Flow 1 Hr after Administration (%) |
|---|---|
| 1 | 34.0 ± 6.1* |
| 21 | 59.4 ± 9.7** |
| 33 | 14.5 ± 4.0 |
| 36 | 15.4 ± 4.5 |
| 47 | 24.3 ± 13.7 |
| EMD57283 | 10.8 ± 4.1 |

*$p < 0.05$,
**$p < 0.01$ vs. EMD57283 (Student's t-test)

It can be seen that each of the compounds of Examples 1, 21, 33, 36, and 47 exhibits more potent activity in increasing the renal blood flow than the reference drug.

TEST EXAMPLE 4

Acute Toxicity

A test compound suspended in 1% (w/v) methyl cellulose aqueous solution was orally administered to three male mice in a single dose of 2 g/kg, and the survival and general conditions were observed for 14 days to obtain $LD_{50}$. The results obtained are shown in Table 9 below.

TABLE 9

| Compound of Example | $LD_{50}$ (g/kg) |
|---|---|
| 1 | >2.0 |
| 2 | >2.0 |
| 33 | >2.0 |

Each of the compounds of Examples 1, 2 and 33 was thus proved highly safe.

TEST EXAMPLE 5

Antianginal Activity

The test was carried out in accordance with the method of Hiramatsu, et al. (see *Japanese Journal of Pharmacology*, Vol. 20, p. 313 (1970)).

Electrodes for ECG were fitted to the extremities of male HOS-Donryu rats (body weight: 300–350 g) under anesthesia with sodium pentobarbital (50 mg/kg, i.p.), and ECG in lead II was recorded. A cannula for blood pressure measurement was inserted into the left femoral artery, and a cannula for drug administration was inserted into the left femoral vein. Thirty minutes after administration of the compound of Example 47, and 5 minutes after administration of nifedipine or cromakalim; 0.5 U/kg of vasopressin (Sigma Chemical Company) was intravaneously administered. Then, ECG was taken every 30 seconds over a period of 5 minutes to observe depression of the ST segment. A control group was given the solvent for the drug (a solution in which 5% dimethyl sulfoxide, 5% polyethylene glycol 200 and 1% cremophor were dissolved in physiological saline). The depression of the ST segment ($\Delta\mu V$) obtained every 30 seconds was connected with a straight line, and the area surrounded by the resulting curve (S value; $\mu V \cdot min$) was taken as the degree of depression in a time period of 5 minutes. Each test compound was given at a dose which reduces the mean blood pressure by about 30 mmHg.

TABLE 10

| Test Compound | Dose (mg/kg, i.v.) | S Value ($\mu V \cdot min$) |
| --- | --- | --- |
| Control | — | 526 |
| Compound of Example 47 | 0.01 | 109** |
| Nifedipine | 0.03 | 393 |
| Cromakalim | 0.01 | 562 |

Note:
**$P < 0.01$ vs. control (Student's t-test)

As is shown in Table 10, the compound of Example 47 significantly reduces the S value, efficiently suppressing the ST depression, and thus shows to have antianginal activity.

TEST EXAMPLE 6

Relaxing Activity in Guinea Pig Tracheae

Male guinea pigs (body weight: 400–650 g) were sacrificed by exsanguination, and tracheae were excised. Tracheal preparations were made as described by Takagi, et al. (see *Chemical Pharmacological Bull.*, Vol. 6, pp. 716–720 (1958).

The tracheal preparation was placed in an organ bath filled with a Tyrode's solution (37° C., under aeration with 95% $O_2$/5% $CO_2$ mixed gas). Tracheal responses were measured isometrically using a transducer "EF-601G" (manufactured by Nihon Koden Kogyo Co., Ltd.) and recorded on a multi-pen recorder "R64 GP" (manufactured by Rika Denki Co., Ltd.). The initial tension in the tracheal preparation was set up at 1 g after the preparation had equilibrated for about 60 minutes, a 30 mM potassium chloride was added to cause contraction. After the contractile response had reached a plateau, a test compound was added cumulatively. For comparison, cromakalim known to have bronchial smooth muscle relaxing activity (see *Japanese Journal of Pharmacology*, Vol. 56, pp. 13–21 (1991)) was used.

The relaxing activity was expressed as a concentration inducing 50% relaxation ($EC_{50}$), taking the relaxation by $10^{-8}$ g/ml of isoproterenol (Sigma Chemical Company) as 100%. The results obtained are shown in Table 11.

TABLE 11

| Relaxing Activity in Guinea Pig Tracheae | |
| --- | --- |
| Example No. of Test Compound | $EC_{50}$ ($\times 10^{-6}$M) |
| 23 | 5.5 |
| 29 | 3.0 |
| 32 | 5.0 |

TABLE 11-continued

| Relaxing Activity in Guinea Pig Tracheae | |
| --- | --- |
| Example No. of Test Compound | $EC_{50}$ ($\times 10^{-6}$M) |
| cromakalim | 49 |

Each of the compounds of Examples 23, 29, and 32 exhibits a more potent activity in relaxing tracheal smooth muscle than cromakalim.

While the invention has been described in detail and with reference to specific examples thereof, it will be apparent to one skilled in the art that various changes and modifications can be made therein without departing from the spirit and scope thereof.

What is claimed is:

1. A diazabicycloalkene compound represented by formula (I):

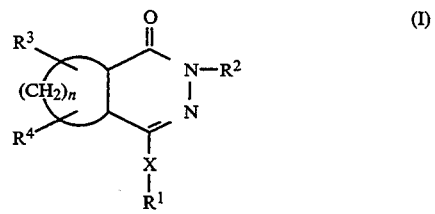

wherein $R^1$ represents a group represented by formula (II) or (III):

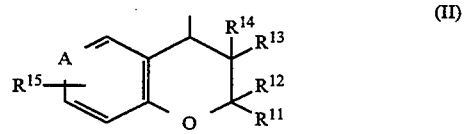

wherein $R^{11}$ and $R^{12}$ each represent a lower alkyl group, or they are taken together to form a lower alkylene group; $R^{13}$ represents a hydroxyl group, a lower acyloxy group or a lower alkoxy group; $R^{14}$ represents a hydrogen atom or a lower alkyl group; A represents a nitrogen atom or C—$R^{16}$; $R^{15}$ and $R^{16}$ each represent a hydrogen atom, a halogen atom, a cyano group, a nitro group, a trifluoromethoxy group, a pentafluoroethyl group, a lower alkyl group, a lower alkenyl group, a lower alkynyl group, a lower acyl group, a carboxyl group, a lower alkoxycarbonyl group, a carbamoyl group which may be substituted with a lower alkyl group having 1 or 2 carbon atoms, a sulfinyl or sulfonyl group which is substituted with a lower alkyl, lower alkoxy, aryl or aryloxy group, or a sulfamoyl group which may be substituted with a lower alkyl group having 1 or 2 carbon atoms:

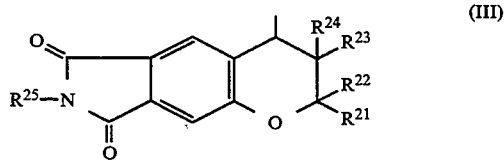

wherein $R^{21}$ and $R^{22}$ each represent a lower alkyl group, or they are taken together to form a lower alkylene group; $R^{23}$ represents a hydroxyl group, a lower acyloxy group or a lower alkoxy group; $R^{24}$ represents a hydrogen atom or a lower alkyl group; $R^{25}$ represents a hydrogen atom, a lower alkyl group, a lower alkenyl group, a lower alkynyl group, an aralkyl group, a pyridylmethyl group, a pyridylethyl group, a pyrimidinylmethyl group, a pyrimidinylethyl group, a piperazinylmethyl group, a piperazinylethyl group, a triazinylmethyl group, a triazinylethyl group, a pyrazolylmethyl group, a pyrazolylethyl group, a pyrazolylpropyl group, an imidazolylmethyl group, an imidazolylethyl group, an imidazolylpropyl group, an oxazolylmethyl group, an oxazolylethyl group, an oxazolylpropyl group, an isoxazolylmethyl group, an isoxazolylethyl group, an isoxazolylpropyl group, a thiazolylmethyl group, a thienylmethyl group, an aziridinylmethyl group, or an aziridinylethyl group; and X represents an oxygen atom, a sulfur atom or N—$R^{31}$, wherein $R^{31}$ represents a hydrogen atom, a lower alkyl group, a lower acyl group or an aralkyl group; $R^2$ represents a hydrogen atom, a lower alkenyl group, a lower alkynyl group, an unsubstituted lower alkyl group, a lower alkyl group substituted with a formyl group, a carboxyl group, a hydroxyl group, a lower alkoxy group, a lower acyl group, a lower alkoxycarbonyl group, a lower acyloxy group, a halogen atom, a nitro group, a cyano group, a lower alkylsulfonyl group, a lower alkylsulfinyl group, an arylsulfonyl group, an arylsulfinyl group, a sulfamoyl group, a mono-lower alkylsulfamoyl group, a di-lower alkylsulfamoyl group, a carbamoyl group, a mono-lower alkylcarbamoyl group, a di-lower alkylcarbamoyl group, an amino group, a mono-lower alkylamino group, a di-lower alkylamino group, a mercapto group, a lower alkylthio group, an arylthio group, a lower acylamino group, or a trifluoromethoxy group, an unsubstituted aryl group, a formylaryl group, a carboxyaryl group, a lower alkoxyaryl group, a lower acylaryl group, a lower alkoxycarbonyl aryl group, a lower acyloxyaryl group, a halogenoaryl group, a nitroaryl group, a cyanoaryl group, a lower alkylsulfonylaryl group, a lower alkylsulfinylaryl group, an arylsulfonylaryl group, an arylsulfinylaryl group, a sulfamoylaryl group, a mono-lower alkylsulfamoylaryl group, a di-lower alkylsulfamoylaryl group, a carbamoylaryl group, a mono-lower alkylcarbamoylaryl group, a di-lower alkylcarbamoylaryl group, an aminoaryl group, a mono-lower alkylaminoaryl group, a di-lower alkylaminoaryl group, a mercaptoaryl group, a lower alkylthioaryl group, an arylthioaryl group, a lower acylaminoaryl group, a trifluoromethoxyaryl group, an unsubstituted aralkyl group, an aralkyl group wherein the aryl moiety is substituted with a halogen atom, a lower alkyl group, a hydroxyl group, a lower alkoxy group, a cyano group, a lower acyl group, a lower alkoxycarbonyl group, a nitro group, a trifluoromethoxy group, a lower alkylsulfinyl group, a lower alkylsulfonyl group, a lower alkoxysulfonyl group, a lower alkoxysulfinyl group, a carbamoyl group, a mono-lower alkylcarbamoyl group, a di-lower alkylcarbamoyl group, a sulfamoyl group, a mono-lower alkylsulfamoyl group, a di-lower alkylsulfamoyl group or a carboxyl group, a pyridylmethyl group, a pyridylethyl group, a pyrimidinylmethyl group, a pyrimidinylethyl group, a piperazinylmethyl group, a piperazinylethyl group, a triazinylmethyl group, a triazinylethyl group, a pyrazolylmethyl group, a pyrazolylethyl group, a pyrazolylpropyl group, an imidazolylmethyl group, an imidazolylethyl group, an imidazolylpropyl group, an oxazolylmethyl group, an oxazolylethyl group, an oxazolylpropyl group, an isoxazolylmethyl group, an isoxazolylethyl group, an isoxazolylpropyl group, a thiazolylmethyl group, a thienylmethyl group, an aziridinylmethyl group, or an aziridinylethyl group; $R^3$ and $R^4$ each represent a hydrogen atom, a halogen atom or a lower alkyl group; and n represents 1 or 2, or a pharmaceutically acceptable salt thereof.

2. The compound of claim 1, wherein $R^1$ is a group represented by formula (II).

3. The compound of claim 1, wherein $R^1$ is a group represented by formula (II), wherein A is C—$R^{16}$; X is an oxygen atom; and n is 1.

4. The compound of claim 1 which is an optically active compound represented by formula (Ia), (Ib), (Ic) or (Id), or a mixture thereof:

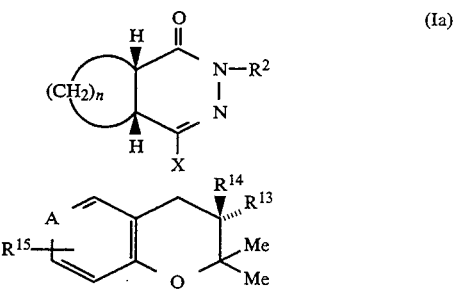

(Ia)

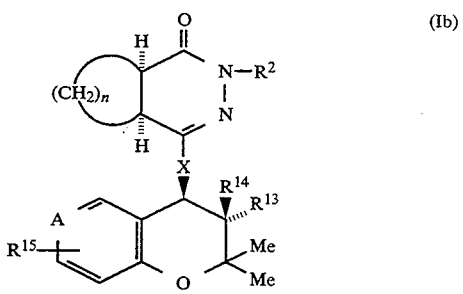

(Ib)

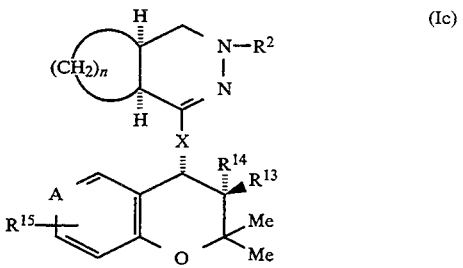

(Ic)

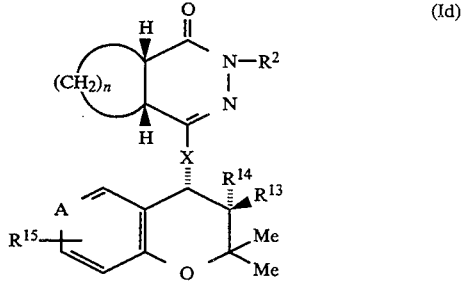

(Id)

wherein $R^2$, $R^{13}$, $R^{14}$, $R^{15}$, A, X, and n are as defined in claim 1.

5. A pharmaceutical composition for the treatment of hypertension, angina pectoris or asthma comprising a diazabicycloalkene compound represented by formula (I):

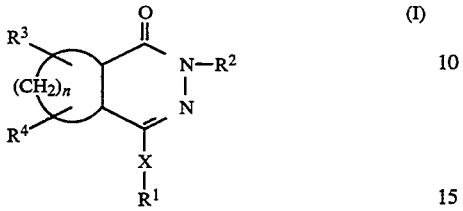

wherein $R^1$ represents a group represented by formula (II) or (III):

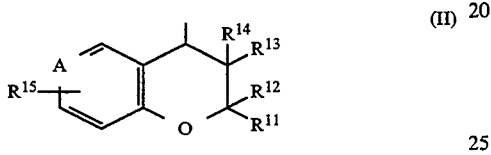

wherein $R^{11}$ and $R^{12}$ each represent a lower alkyl group, or they are taken together to form a lower alkylene group; $R^{13}$ represents a hydroxyl group, a lower acyloxy group or a lower alkoxy group; $R^{14}$ represents a hydrogen atom or a lower alkyl group; A represents a nitrogen atom or C—$R^{16}$; $R^{15}$ and $R^{16}$ each represent a hydrogen atom, a halogen atom, a cyano group, a nitro group, a trifluoromethoxy group, a pentafluoroethyl group, a lower alkyl group, a lower alkenyl group, a lower alkynyl group, a lower acyl group, a carboxyl group, a lower alkoxycarbonyl group, a carbamoyl group which may be substituted with a lower alkyl group having 1 or 2 carbon atoms, a sulfinyl or sulfonyl group which is substituted with a lower alkyl, lower alkoxy, aryl or aryloxy group, or a sulfamoyl group which may be substituted with a lower alkyl group having 1 or 2 carbon atoms:

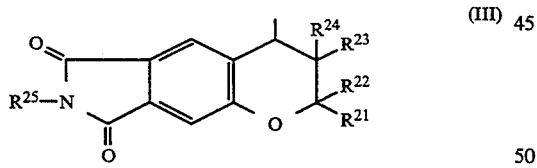

wherein $R^{21}$ and $R^{22}$ each represent a lower alkyl group, or they are taken together to form a lower alkylene group; $R^{23}$ represents a hydroxyl group, a lower acyloxy group or a lower alkoxy group; $R^{24}$ represents a hydrogen atom or a lower alkyl group; $R^{25}$ represents a hydrogen atom, a lower alkyl group, a lower alkenyl group, a lower alkynyl group, an aralkyl group, a pyridylmethyl group, a pyridylethyl group, a pyrimidinylmethyl group, a pyrimidinylethyl group, a piperazinylmethyl group, a piperazinylethyl group, a triazinylmethyl group, a triazinylethyl group, a pyrazolylmethyl group, a pyrazolylethyl group, a pyrazolylpropyl group, an imidazolylmethyl group, an imidazolylethyl group, an imidazolylpropyl group, an oxazolylmethyl group, an oxazolylethyl group, an oxazolylpropyl group, an isoxazolylmethyl group, an isoxazolylethyl group, an isoxazolylpropyl group, a thiazolylmethyl group, a thienylmethyl group, an aziridinylmethyl group, or an aziridinylethyl group; and X represents an oxygen atom, a sulfur atom or N—$R^{31}$, wherein $R^{31}$ represents a hydrogen atom, a lower alkyl group, a lower acyl group or an aralkyl group; $R^2$ represents a hydrogen atom, a lower alkenyl group, a lower alkynyl group, an unsubstituted lower alkyl group, a lower alkyl group substituted with a formyl group, a carboxyl group, a hydroxyl group, a lower alkoxy group, a lower acyl group, a lower alkoxycarbonyl group, a lower acyloxy group, a halogen atom, a nitro group, a cyano group, a lower alkylsulfonyl group, a lower alkylsulfinyl group an arylsulfonyl group, an arylsulfinyl, group, a sulfamoyl group, a mono-lower alkylsulfamoyl group, a di-lower alkylsulfamoyl group, a carbamoyl group, a mono-lower alkylcarbamoyl group, a di-lower alkylcarbamoyl group, an amino group, a mono-lower alkylamino group, a di-lower acylamino group, a mercapto group, a lower alkylthio group, an arylthio group, a lower acylamino group, or a trifluoromethoxy group, an unsubstituted aryl group, a formylaryl group, a carboxyaryl group, a lower alkoxyaryl group, a lower acylaryl group, a lower alkoxycarbonylaryl group, a lower acyloxyaryl group, a halogenoaryl group, a nitroaryl group, a cyanoaryl group, a lower alkylsulfonylaryl group, a lower alkylsulfinylaryl group, an arylsulfonylaryl group, an arylsulfinylaryl group, a sulfamoylaryl group, a mono-lower alkylsulfamoylaryl group, a di-lower alkylsulfamoylaryl group, a carbamoylaryl group, a mono-lower alkylcarbamoylaryl, group, a di-lower alkylcarbamoylaryl group, an aminoaryl group, a mono-lower alkylaminoaryl group, a di-lower alkylaminoaryl group, a mercaptoaryl group, a lower alkylthioaryl group, an arylthioaryl group, a lower acylaminoaryl group, a trifluoromethoxyaryl group, an unsubstituted aralkyl group, an aralkyl group wherein the aryl moiety is substituted with a halogen atom, a lower alkyl group, a hydroxyl group, a lower alkoxy group, a cyano group, a lower acyl group, a lower alkoxycarbonyl group, a nitro group, a trifluoromethoxy group, a lower alkylsulfinyl group, a lower alkylsulfonyl group, a lower alkoxysulfonyl group, a lower alkoxysulfinyl group, a carbamoyl group, a mono-lower alkylcarbamoyl group, a di-lower alkylcarbamoyl group, a sulfamoyl group, a mono-lower alkylsulfamoyl group, a di-lower alkylsulfamoyl group or a carboxyl group, a pyridylmethyl group, a pyridylethyl group, a pyrimidinylmethyl group, a pyrimidinylethyl group, a piperazinylmethyl group, a piperazinylethyl group, a triazinylmethyl group, a triazinylmethyl group, a pyrazolylmethyl group, a pyrazolylethyl group, a pyrazolylpropyl group, an imidazolylmethyl group, an imidazolylethyl group, an imidazolylpropyl group, an oxazolylmethyl group, an oxazolylethyl group, an oxazolylpropyl group, an isoxazolylmethyl group, an isoxazolylethyl group, an isoxazolylpropyl group, a thiazolylmethyl group, a thienylmethyl group, an aziridinylmethyl group, or an aziridinylethyl group; $R^3$ and $R^4$ each represent a hydrogen atom, a halogen atom or a lower alkyl group; and n represents 1 or 2, or a pharmaceutically acceptable salt thereof as an active ingredient, together with a pharmaceutically acceptable carrier.

6. The composition as claimed in claim 5, wherein said diazabicycloalkene compound is an optically active compound represented by formula (Ia), (Ib), (Ic) or (Id):

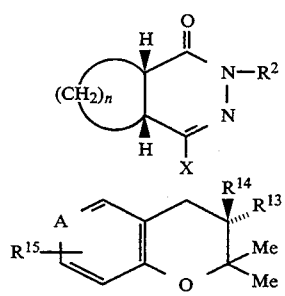
(Ia)

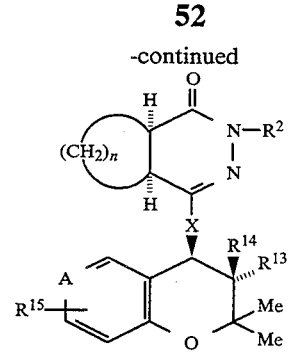
(Ib)

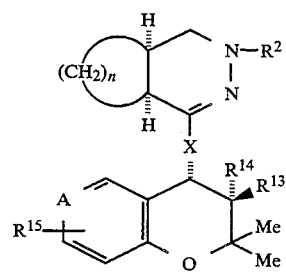
(Ic)

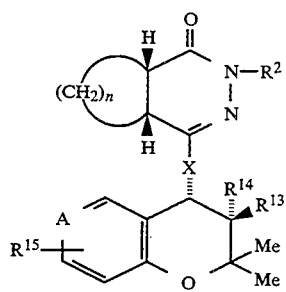
(Id)

wherein $R^2$, $R^{13}$, $R^{14}$, $R^{15}$, A, X, and n are as defined in claim 5, or a mixture thereof, or a pharmaceutically acceptable salt thereof.

* * * * *

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 6, lines 30-40, delete

"
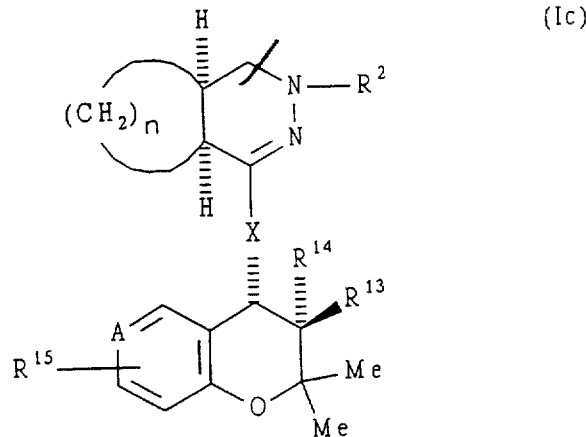
"

and insert therefor

--
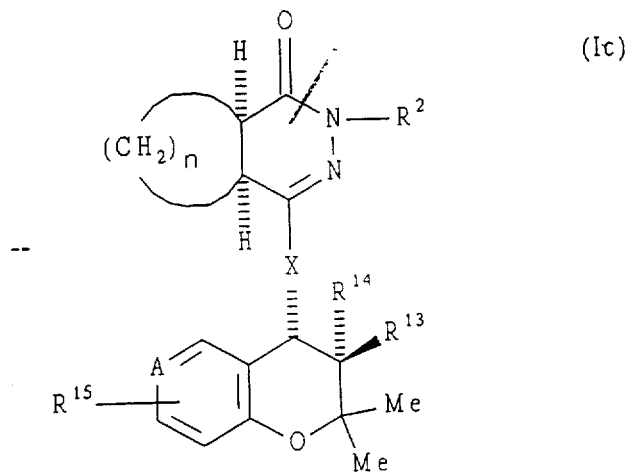
--.

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 12, lines 40-53, delete

"
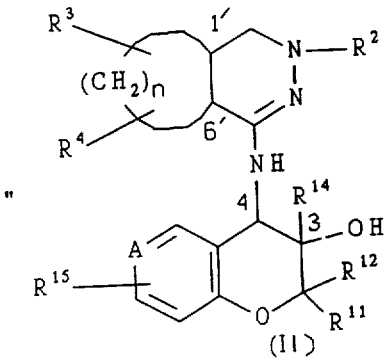 or 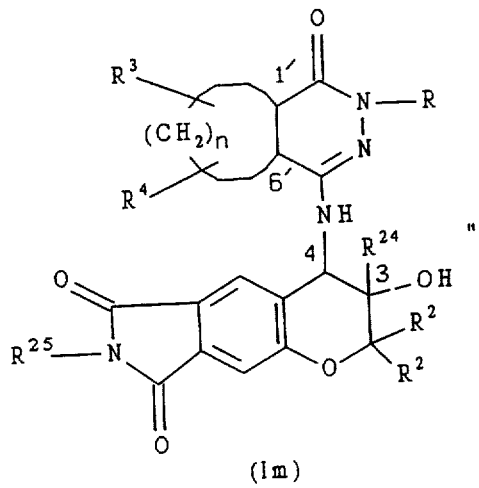
"

and insert therefor

--
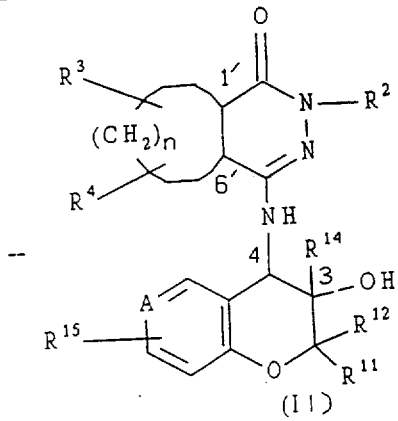 or 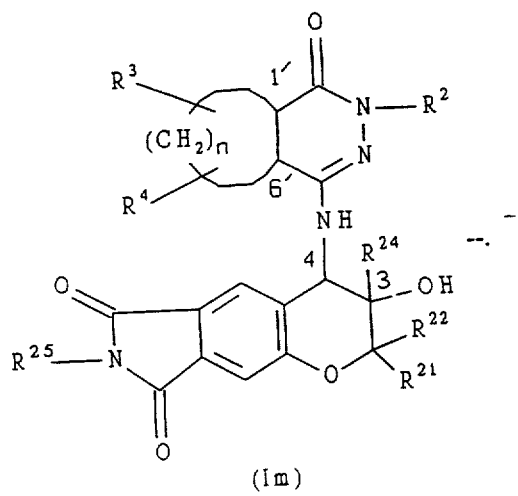
--.

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Columns 15 and 16, Table 1, delete

"9  (±)-3-(2,2-diethoxyethyl)-3,4-diazabicyclo[4.1.0]heptane-2,5-dione    83-84    1.20-3.30(7H, m), 1.70(1H, m),2.10-2.30(2H, m), 3.50-3.64(3H, m), 3.18-3.82(2H, m), 3.91(1H, dd, J=14.7, 3.9Hz), 4.59(1H, dd, J=5.9, 3.9Hz), 8.16(1H,s)"

and insert therefor

--9  (±)-3-(2,2-diethoxyethyl)-3,4-diazabicyclo[4.1.0]heptane-2,5-dione    83-84    1.20-3.30(7H, m), 1.70(1H, m),2.10-2.30(2H, m), 3.50-3.64(3H, m), 3.68-3.82(2H, m), 3.91(1H, dd, J=14.7, 3.9Hz), 4.59(1H, dd, J=5.9, 3.9Hz), 8.16(1H,s)--.

Column 17, Table 1, delete

"23  (±)-3-(2-methyl-2-propen-1-yl)-3,4-diazabicyclo[4.1.0]heptane-215-dione"

and insert therefor

--23  (±)-3-(2-methyl-2-propen-1-yl)-3,4-diazabicyclo[4.1.0]heptane-2,5-dione--.

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 31, Table 3, delete

"22   (3S,4R,1'R*,6'S*)-3,4-dihydro-2,2-dimethyl-3-hydroxy-4-(3-methyl-2-oxo-3,4-diazabicyclo-(4.1.0]hept-4-en-5-yloxy)-2H-benzopyran-6-carbonitrile"

and insert therefor

--22   (3S,4R,1'R*,6'S*)-3,4-dihydro-2,2-dimethyl-3-hydroxy-4-(3-methyl-2-oxo-3,4-diazabicyclo-[4.1.0]hept-4-en-5-yloxy)-2H-1-benzopyran-6-carbonitrile--.

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Columns 31 and 32, Table 3, delete

"25  3S,4R,1'R*,6'S*)-3,4-dihydro-2,2-dimethyl-3-hydroxy-4-(3-(2-methoxyethyl)-2-oxo-3,4-diazabicyclo(4.1.0]hept-4-en-5-yloxy)-2H-1-benzopyran-6-carbonitrile   0.50 ($CHCl_3$/MeOH =10:1, v/v)   -165.0   1.03(1H, m), 1.33(3H, 2), 1.51(3H, 2), 1.72(1H, m), 2.20(1H, m), 229(1H,m), 3.35(1H, s), 3.57(1H, m), 3.63-3.69(2H, m), 3.88(1H, dd, J=4.9, 7.8Hz), 3.96(1H, m), 3.99(1H, d, J=4.9Hz), 5.82(1H, d, J=7.8Hz), 6.90(1H, d, J=8.3Hz), 7.50(1H, dd, J=2.0, 8.3Hz), 7.64(1H, d, J=2.0Hz)"

and insert therefor

--25  (3S,4R,1'R*,6'S*)-3,4-dihydro-2,2-dimethyl-3-hydroxy-4-(3-(2-methoxyethyl)-2-oxo-3,4-diazabicyclo[4.1.0]hept-4-en-5-yloxy)-2H-1-benzopyran-6-carbonitrile   0.50 ($CHCl_3$/MeOH =10:1, v/v)   -165.0   1.03(1H, m), 1.33(3H, s), 1.51(3H, s), 1.72(1H, m), 2.20(1H, m), 2.29(1H,m), 3.35(1H, s), 3.57(1H, m), 3.63-3.69(2H, m), 3.88(1H, dd, J=4.9, 7.8Hz), 3.96(1H, m), 3.99(1H, d, J=4.9Hz), 5.82(1H, d, J=7.8Hz), 6.90(1H, d, J=8.3Hz), 7.50(1H, dd, J=2.0, 8.3Hz), 7.64(1H, d, J=2.0Hz)--.

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 33, Table 3, delete

"31   (3S,4R,1'R*,6'S*)-3,4-dihydro-2,2-dimethyl-3-hydroxy-4-(3-isobutyl-2-oxo-3,4-diazabicyclo-(4.1.0]hept-4-en-5-yloxy)-2H-1-benzopyran-6-carbonitrile 32   (3S,4R,1'R*,6'S*)-4-3-n-butyl-2-oxo-3,4-diazabicyclo(4.1.0]-hept-4-en-5-yloxy)-3,4-dihydro-2,2-dimethyl-3-hydroxy-2H-1-benzopyran-6-carbonitrile"

and insert therefor

--31   (3S,4R,1'R*,6'S*)-3,4-dihydro-2,2-dimethyl-3-hydroxy-4-(3-isobutyl-2-oxo-3,4-diazabicyclo-[4.1.0]hept-4-en-5-yloxy)-2H-1-benzopyran-6-carbonitrile 32   (3S,4R,1'R*,6'S*)-4-3-n-butyl-2-oxo-3,4-diazabicyclo[4.1.0]-hept-4-en-5-yloxy)-3,4-dihydro-2,2-dimethyl-3-hydroxy-2H-1-benzopyran-6-carbonitrile--.

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 33, Table 3, delete

"35  (3S,4R,1'R*,6'S*)-4-(3-(4-chlorobenzyl-2-oxo-3,4-diaza-bicyclo(4.1.0]hept-4-en-5-yl-oxy)-3,4-dihydro-2,2-dimethyl-3-hydroxy-2H-1-benzopyran-6-carbonitrile"

and insert therefor

--35  (3S,4R,1'R*,6'S*)-4-(3-(4-chlorobenzyl)-2-oxo-3,4-diaza-bicyclo[4.1.0]hept-4-en-5-yl-oxy)-3,4-dihydro-2,2-dimethyl-3-hydroxy-2H-1-benzopyran-6-carbonitrile--.

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below: Column 37, Table 3, delete "44 (3S,4R,1'R*,6'S*)-3,4-dihydro-2,2-dimethyl-3-hydroxy-4-(2-oxo-3-(4-sulfamoylbenzyl)-3,4-diazabicyclo(4.1.0)hept-4-en-5-yloxy)-2H-1-benzopyran-6-carbonitrile 45 (3S,4R,1'R*,6'S*)-3,4-dihydro-2,2-dimethyl-4-(3-(2-fluoro-benzyl)-2-oxo-3,4-diazabicyclo-4.1.0]hept-4-en-5-yloxy)-3-hydroxy-2H-1-benzopyran-6-carbonitrile"

and insert therefor

--44 (3S,4R,1'R*,6'S*)-3,4-dihydro-2,2-dimethyl-3-hydroxy-4-(2-oxo-3-(4-sulfamoylbenzyl)-3,4-diazabicyclo[4.1.0]hept-4-en-5-yloxy)-2H-1-benzopyran-6-carbonitrile 45 (3S,4R,1'R*,6'S*)-3,4-dihydro-2,2-dimethyl-4-(3-(2-fluoro-benzyl)-2-oxo-3,4-diazabicyclo-[4.1.0]hept-4-en-5-yloxy)-3-hydroxy-2H-1-benzopyran-6-carbonitrile--

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo It is certified that error appears in the above-identified patent and that said Letters Patent is hereby corrected as shown below:

Column 39, Table 4, delete

"49 (3S,4R,1'R*,6'S*)-3,4-dihydro-2,2-dimethyl-4-(3-ethoxy-carbonylmethyl-2-oxo-3,4-diazabicyclo(4.1.0]hept-4-en-5-yloxy)-3-hydroxy-2H-1-benzo-pyran-6-carbonitrile"

and insert therefor

--49 (3S,4R,1'R*,6'S*)-3,4-dihydro-2,2-dimethyl-4-(3-ethoxy-carbonylmethyl-2-oxo-3,4-diazabicyclo[4.1.0]hept-4-en-5-yloxy)-3-hydroxy-2H-1-benzo-pyran-6-carbonitrile--.

Column 41, line 51, delete "d!" and insert therefor --d,--.

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Column 48, lines 22-34, delete

"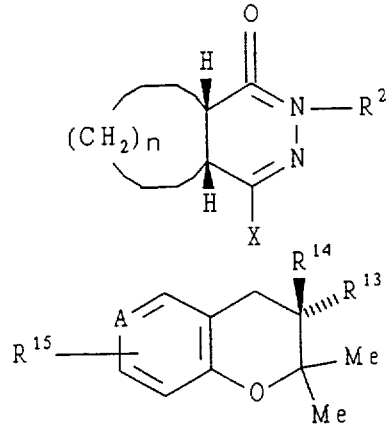"

and insert therefor

--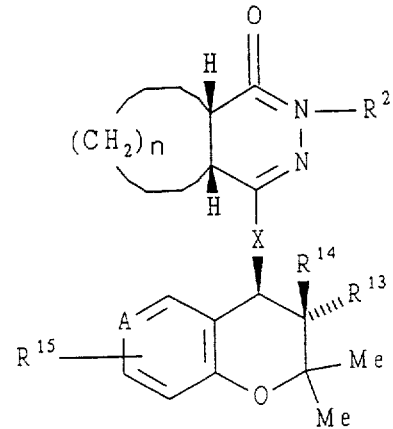--;

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Column 48, lines 46-56, delete

"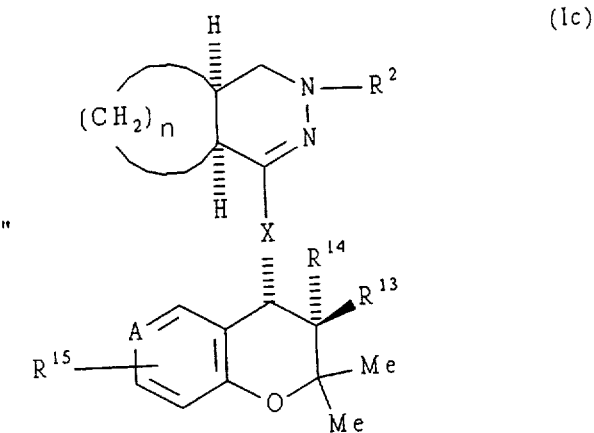"

and insert therefor

--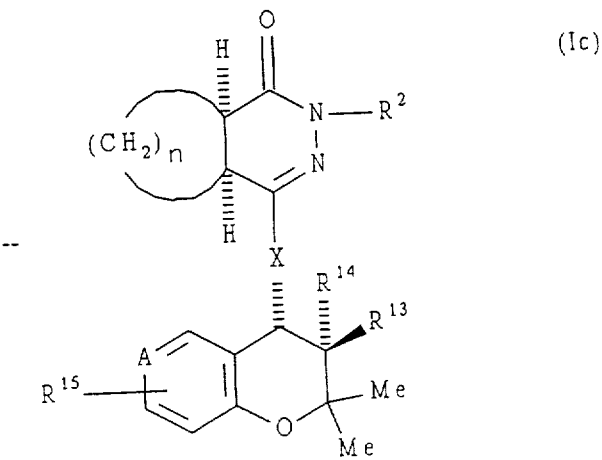--.

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Column 51, lines 24-38, delete

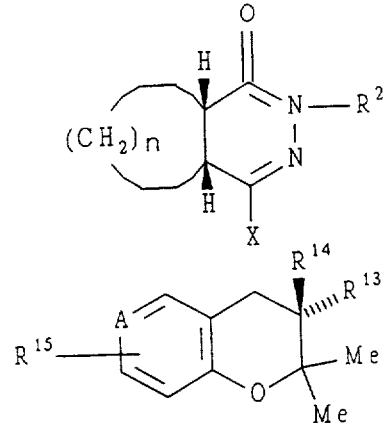

"

and insert therefor

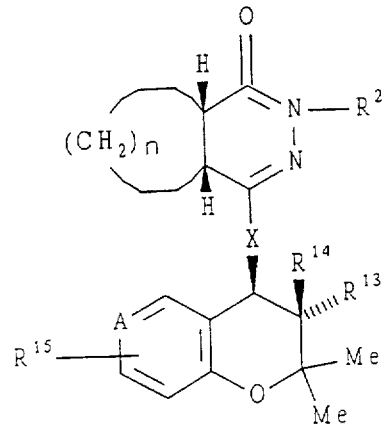

--.

UNITED STATES PATENT AND TRADEMARK OFFICE
CERTIFICATE OF CORRECTION

PATENT NO. : 5,418,232

DATED : May 23, 1995

INVENTOR(S) : Tetsuya Mimura, Hideo Kubo

It is certified that error appears in the above-identified patent and that said Letters Patent is hereby corrected as shown below:

Column 52, lines 14-24, delete

"
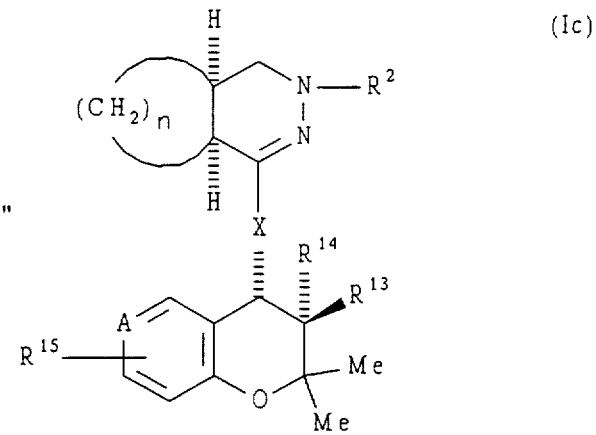
"

UNITED STATES PATENT AND TRADEMARK OFFICE
CERTIFICATE OF CORRECTION

PATENT NO. : 5,418,232
DATED : May 23, 1995
INVENTOR(S) : Tetsuya Mimura, Hideo Kubo Page 14 of 14

It is certified that error appears in the above-indentified patent and that said Letters Patent is hereby corrected as shown below:

and insert therefor

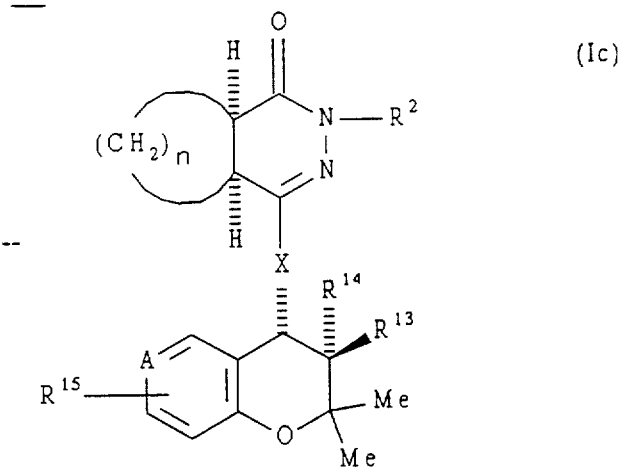

Signed and Sealed this

Thirteenth Day of August, 1996

Attest:

BRUCE LEHMAN

Attesting Officer     Commissioner of Patents and Trademarks